(12) United States Patent
Duffy

(10) Patent No.: US 11,833,046 B2
(45) Date of Patent: Dec. 5, 2023

(54) DELIVERY CATHETER SYSTEM

(71) Applicant: Medtronic Vascular, Inc., Santa Rosa, CA (US)

(72) Inventor: Niall F. Duffy, Tuam (IE)

(73) Assignee: Medtronic Vascular, Inc., Santa Rosa, CA (US)

(*) Notice: Subject to any disclaimer, the term of this patent is extended or adjusted under 35 U.S.C. 154(b) by 200 days.

(21) Appl. No.: 17/391,503

(22) Filed: Aug. 2, 2021

(65) Prior Publication Data

US 2022/0061987 A1    Mar. 3, 2022

Related U.S. Application Data

(60) Provisional application No. 63/070,556, filed on Aug. 26, 2020.

(51) Int. Cl.

| A61F 2/966 | (2013.01) |
|---|---|
| A61F 2/24 | (2006.01) |
| A61F 2/95 | (2013.01) |
| A61M 25/01 | (2006.01) |

(52) U.S. Cl.
CPC .......... *A61F 2/2436* (2013.01); *A61F 2/9517* (2020.05); *A61F 2/966* (2013.01); *A61M 25/0122* (2013.01); *A61M 2210/125* (2013.01)

(58) Field of Classification Search
CPC .......... A61F 2/962; A61F 2/966; A61F 2/011; A61F 2002/9665; A61F 2/2427; A61F 2/243; A61F 2/2433; A61F 2/2439; A61F 2/95; A61F 2/9517; A61F 2/9522; A61F 2/9524; A61F 2/9525; A61F 2/9526; A61F 2/954; A61F 2/958; A61F 2/1662;
(Continued)

(56) References Cited

U.S. PATENT DOCUMENTS

| 9,579,198 B2 | 2/2017 | Deem et al. |
|---|---|---|
| 2018/0296325 A1 | 10/2018 | Mclean |
| 2018/0325660 A1 | 11/2018 | Taylor et al. |

(Continued)

FOREIGN PATENT DOCUMENTS

| WO | 2014/121280 A2 | 8/2014 |
|---|---|---|
| WO | 2018/162317 A2 | 9/2018 |

OTHER PUBLICATIONS

International Search Report and Written Opinion, International Application No. PCT/US2021/047428, dated Mar. 11, 2022.

*Primary Examiner* — Timothy J Neal
*Assistant Examiner* — Moira E Hayes
(74) *Attorney, Agent, or Firm* — Medler Ferro Woodhouse & Mills PLLC

(57) ABSTRACT

A delivery system for prosthetic medical devices. The delivery system may include a delivery system configured to be driven between a containment configuration and a deployment configuration. The delivery system may be configured to cause relative motion between a delivery capsule and a prosthetic device within the delivery capsule. The delivery system may include a first fluid pathway and a second fluid pathway and may be configured to switch between the first fluid pathway and the second fluid pathway as the delivery system transitions toward a deployment configuration. The delivery system may include a recapture circuit configured to enable the delivery system to recapture a prosthetic device using the delivery capsule.

20 Claims, 10 Drawing Sheets

(58) Field of Classification Search
CPC ...... A61F 2/1667; A61F 2/167; A61F 2/1672; A61F 2/1675; A61F 2/1678
See application file for complete search history.

(56) References Cited

U.S. PATENT DOCUMENTS

| | | | |
|---|---|---|---|
| 2018/0333253 A1* | 11/2018 | Zakay | A61F 2/167 |
| 2020/0261226 A1* | 8/2020 | Dueri | A61F 2/2427 |
| 2020/0345489 A1 | 11/2020 | Duffy et al. | |

* cited by examiner

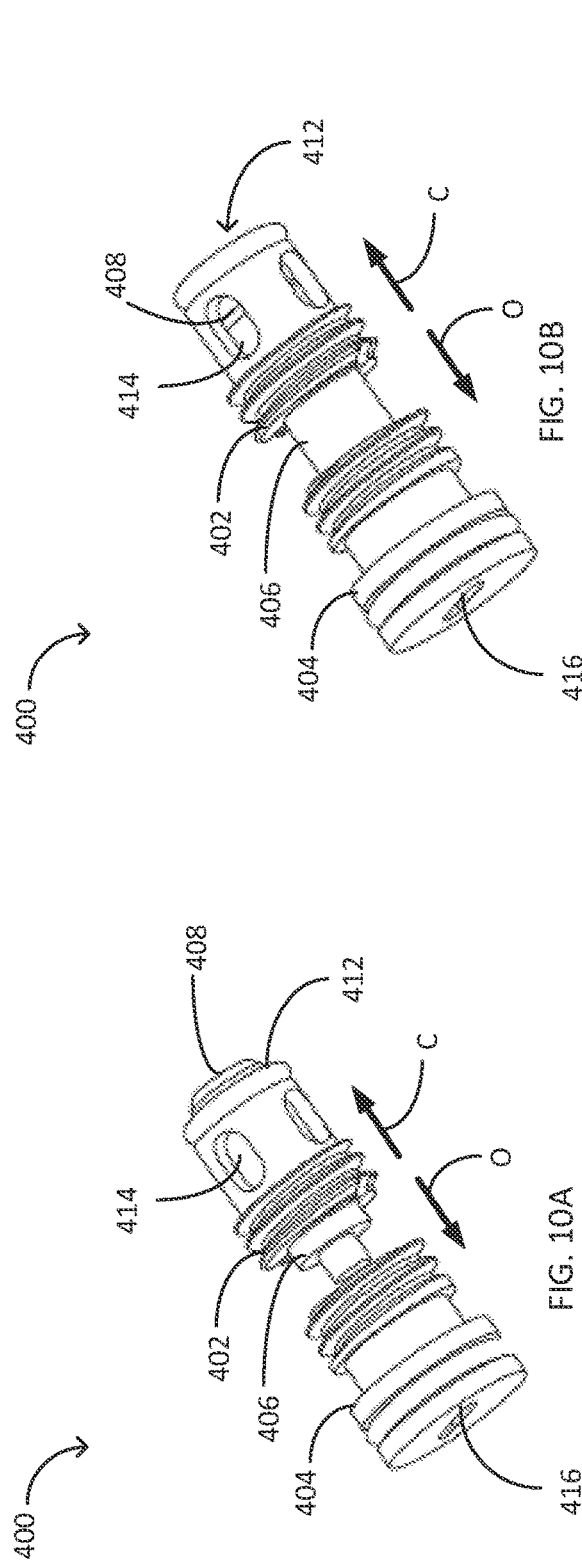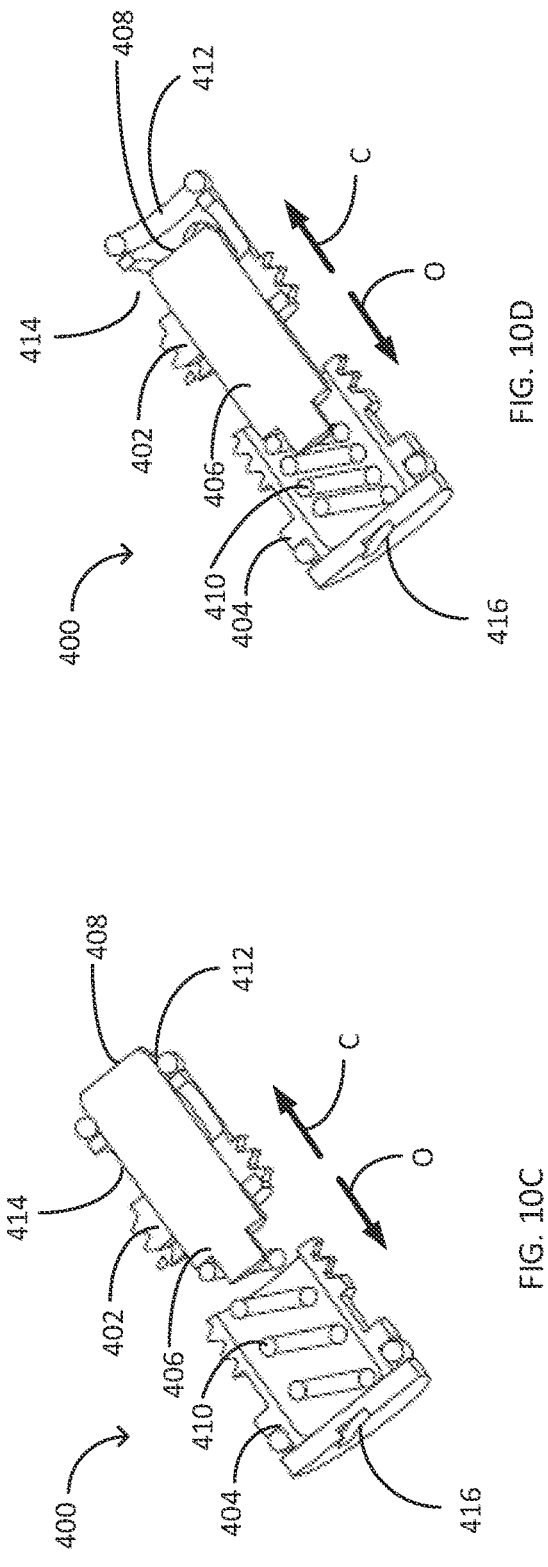

DELIVERY CATHETER SYSTEM

CROSS-REFERENCE TO RELATED APPLICATIONS

This application claims the benefit of the filing date of U.S. Provisional Application No. 63/070,556, filed Aug. 26, 2020, the contents of which are incorporated by reference herein in their entirety.

TECHNICAL FIELD

The disclosure relates generally to systems, devices, methods, and techniques for delivery of medical devices, such as, for example, prosthetic implants, such as, for example, prosthetic heart valves.

BACKGROUND

Devices used to repair heart valves are one example of a category of medical devices to which this disclosure relates, although this disclosure also relates to the delivery of other medical devices. With respect to that example, native heart valves can be affected by several medical conditions. For example, mitral valves can be affected by mitral valve regurgitation, mitral valve prolapse and mitral valve stenosis. One method of treatment includes replacement of the heart valve by implanting a prosthetic heart valve into the heart in place of the native mitral valve. Another method of treatment includes repair, bypassing, or replacement of a previously implanted prosthetic heart valve. In some cases, one or more prosthetic heart valves may be implanted percutaneously using valve delivery devices. In some cases, a prosthetic heart valve may be sheathed within a capsule to allow for the percutaneous delivery via a catheter, with the prosthetic heart valve assuming a relatively small cross-sectional dimension in the fully sheathed configuration. In some cases, once delivered and placed in the target site, the prosthetic heart valve device may be unsheathed to expand to assume a larger cross-sectional dimension. In some cases, before transitioning to the prosthetic heart valve to an unsheathed condition at the target site, alignment of the prosthetic heart valve within the patient may be evaluated using imaging techniques.

SUMMARY

In some examples, a delivery system for a prosthetic heart valve device includes a delivery system configured to be hydraulically driven between a containment configuration for holding the prosthetic heart valve device and a deployment configuration for at least partially deploying the prosthetic heart valve device. In some examples, a delivery system defines a hydraulic circuit including a first fluid pathway and a second fluid pathway. In some examples, a delivery system is configured such that a hydraulic delivery of a deployment fluid along the first fluid pathway drives the delivery system from the containment configuration towards a first partial deployment configuration, and drives a stop pin from a first pin position to a second pin position. In some examples, in a first pin position, the deployment fluid flows along a first fluid pathway. In some examples, in a second pin position the deployment fluid is blocked from flowing along the first fluid pathway, and a valve directs the deployment fluid through a second flow pathway.

In some examples, a delivery system for a prosthetic heart valve includes a delivery system configured to be hydraulically driven between a containment configuration for holding the prosthetic heart valve device and a deployment configuration for at least partially deploying the prosthetic heart valve device. In some examples, a delivery system defines a hydraulic circuit including a first fluid pathway and a second fluid pathway. In some examples, a delivery system is configured such that hydraulic delivery of a deployment fluid along the first fluid pathway drives a delivery system from the containment configuration towards a first partial deployment configuration, and drives a stop pin from a first pin position in which the deployment fluid flows along the first fluid pathway to a second pin position in which the deployment fluid is blocked from flowing along the first fluid pathway. In some examples, when a stop pin is in a second pin position, the deployment fluid is directed via a valve through a second flow pathway. In some examples, the delivery system is configured to hold a prosthetic heart valve device in a first partial deployment configuration when a stop pin is in a second pin position and until the valve directs the deployment fluid through a second fluid pathway. In some examples, a delivery system is configured to drive a stop pin from a second pin position to a third pin position in which a deployment fluid flows along a first fluid pathway.

In some examples, a technique includes providing a fluid flow through a first fluid pathway in a hydraulic circuit defined by a delivery system. In some examples, a technique includes driving a delivery system from a containment configuration toward a first partial deployment configuration using fluid flow through a first fluid pathway. In some examples, a technique includes driving a stop pin from a first pin position to a second pin position using fluid flow through a first fluid pathway, blocking fluid flow through a first fluid pathway using a stop pin in a second pin position and directing a fluid flow through a second fluid pathway in a hydraulic circuit using a valve, and driving a delivery system toward a deployment configuration using fluid flow through a second fluid pathway.

The details of one or more examples are set forth in the accompanying drawings and the description below. Other features, objects, and advantages will be apparent from the description and drawings, and from the claims.

BRIEF DESCRIPTION OF DRAWINGS

FIG. 10A is a schematic illustration of an example valve in a first position.

FIG. 10B is a schematic illustration of the valve of FIG. 10A in a second position.

FIG. 10C is a cross-sectional view of the valve of FIG. 10A.

FIG. 10D is a cross-sectional view of the valve of FIG. 10B.

DETAILED DESCRIPTION

Figure 1:
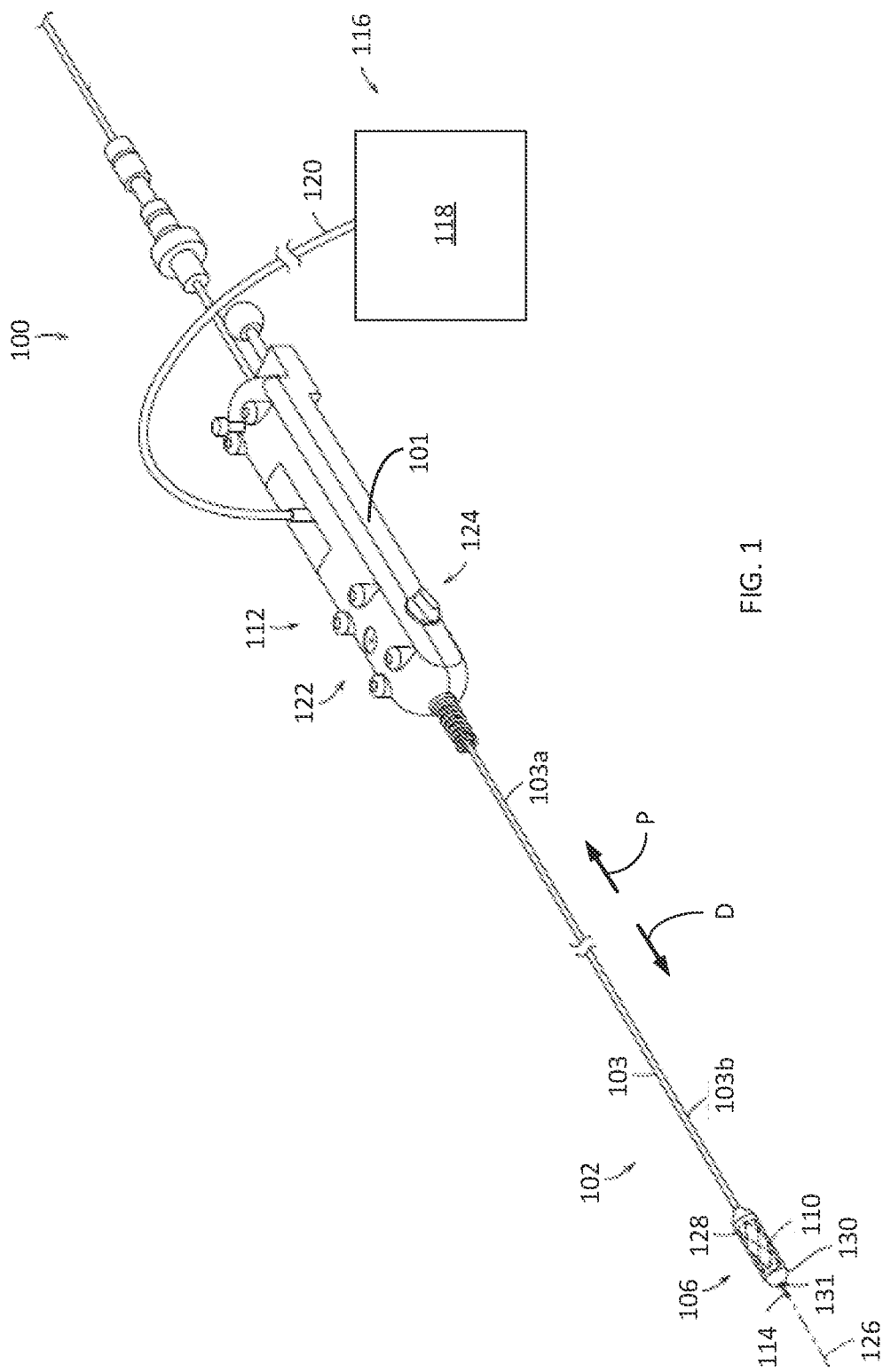
FIG. 1 is an isometric view of an example system for delivering an example prosthetic heart valve device.

Prosthetic heart valve devices may be introduced into a lumen of a body vessel via catheterization techniques, including via percutaneous catheterization techniques. Prosthetic heart valve devices may be configured within a delivery capsule having a relatively small cross-sectional dimension to allow for delivery to a treatment site via a catheter, including to allow for percutaneous delivery. Once the prosthetic heart valve device and delivery capsule are delivered to the target site, a clinician may cause the capsule to unsheathe the prosthetic heart device from the delivery capsule in stages, during which the prosthetic heart valve device expands to assume a larger cross-sectional dimension. In the expanded state, the prosthetic heart valve device may have a larger cross-sectional dimension than the catheter and/or the capsule used for delivery. Consequently, before and during transition of the prosthetic heart valve to an unsheathed condition, alignment of the prosthetic heart valve within the patient may be evaluated using imaging techniques. In some cases, the clinician may determine the prosthetic heart valve device and delivery capsule should be withdrawn from the target site prior to or during the unsheathing.

In some cases, a device delivery system is configured to affect movement of a housing of the delivery capsule ("capsule housing") relative to the prosthetic heart valve in order to sequentially unsheathe the prosthetic heart valve at the target site. For example, the device delivery system may be configured to partially or fully deploy the prosthetic heart valve device by causing the capsule housing to move proximally relative to some portion of the prosthetic heart valve device. As the capsule housing moves distally and begins to unsheathe the prosthetic heart valve device, the prosthetic heart valve device may begin to expand and transition toward a fully deployed configuration. The device delivery system may be configured to allow recapture of the prosthetic heart valve using the capsule housing, such that the prosthetic heart valve device and the delivery capsule may be percutaneously withdrawn from the target site if the clinician desires.

Such procedures may benefit from device delivery systems which provide an ability to translate the capsule housing both distally and proximally relative to the prosthetic heart valve device. Further, such procedures may benefit from a device delivery system configured to provide one or more points during the unsheathing process where the capsule housing and the prosthetic heart valve device are fully, substantially, or partly static relative to one another or relative to some other reference marker, such that the clinician may more easily evaluate the deployment of the prosthetic heart valve device at the one or more points. In some examples, a substantially static posture of the capsule housing and prosthetic heart valve device relative at the one or more points may allow, for example, evaluation of the alignment of the prosthetic heart valve device, or evaluation of whether the prosthetic heart valve device should be recaptured.

In some examples, the disclosure relates to a system for a prosthetic heart valve device. In some examples, a system includes a delivery system configured to control the deployment of a prosthetic heart valve device from a capsule housing. In some examples, a delivery system may be configured to control a recapture of the prosthetic heart valve device using a capsule housing. For example, the delivery system may be configured to cause the capsule housing to move in a proximal direction relative to some portion of the prosthetic heart valve device to gradually unsheathe the prosthetic heart valve device during deployment. In some examples, a delivery system may be configured to cause the capsule housing to move in a distal direction relative to the portion of the prosthetic heart valve device to gradually re-sheathe the prosthetic heart valve device during recapture.

In some examples, a delivery system may be configured to establish and transition among a containment configuration, one or more partial deployment configurations, and a deployment configuration. In some examples, a delivery system may be configured such that, in a containment configuration, a capsule housing fully, substantially, or partly surrounds (e.g., sheathes) a prosthetic heart valve device, such that a capsule housing constrains a prosthetic heart valve device from expanding. In some examples, a delivery system may be configured such that, in one or more partial deployment configurations, capsule housing surrounds only a portion of the prosthetic heart valve device (e.g., a proximal portion), such that a capsule housing constrains only the portion of the prosthetic heart valve device from expanding while allowing the remaining portion of the prosthetic heart valve to expand without constraint by the capsule housing. In some examples, a delivery system may be configured such that, in a deployed configuration, a capsule housing assumes a position whereby a capsule housing offers lower or substantially no impact of the expansion of the prosthetic heart valve device compared to other possible capsule housings, such that a prosthetic heart valve device may expand subject to less constraint by the capsule housing. In some examples, a delivery system is configured to transition from a containment configuration to one or more of the partial deployment configurations, and from one or more of the partial deployment configurations to a deployed configuration. In some examples, a delivery system is configured to transition from a partial deployment configuration to a containment configuration (e.g., during recapture of a prosthetic heart valve device).

In some examples, a delivery system may be configured to be hydraulically driven during a valve deployment procedure. For example, a delivery system may be configured to transition from a containment configuration, to a partial deployment configuration and to a deployment configuration using a first fluid pathway and a second fluid pathway. In some examples, a delivery system defines a first fluid pathway and a second fluid pathway. In some examples, a delivery system is configured such that a pressurized fluid may hydraulically drive a delivery system via a first fluid pathway and a second fluid pathway and cause a delivery system to substantially establish a containment configuration, one or more of partial deployment configurations, and/or a deployment configuration. In some examples, a delivery system is configured to switch the delivery of a pressurized fluid from a first fluid pathway to a second fluid pathway, and vice-versa, as a delivery system achieves and transitions out of at least one partial deployment configuration and continues toward a deployment configuration.

In some examples, a delivery system may be configured to at least momentarily stop (e.g., pause) relative motion between a capsule housing and a prosthetic heart valve device when the delivery of the pressurized fluid switches from the first fluid pathway to a second fluid pathway (and vice-versa). In some examples, a delivery system is configured such that the pathway switch and a resulting stop substantially coincide with a delivery system establishing at least one partial deployment configuration. Coinciding the stop with one or more of the partial deployment configurations may allow improved evaluation of a prosthetic heart valve device during a procedure. The delivery system may be configured to stop relative motion at one or more partial deployment configurations. In some examples, a delivery system is configured to stop at a first partial deployment configuration where a limited expansion of a partially unsheathed prosthetic heart valve device allows repositioning of a prosthetic heart valve device and a capsule housing within the patient. In some examples, a delivery system may be configured to stop at a second partial deployment configuration where further expansion of a prosthetic heart valve (e.g., due to continued unsheathing) may increase the difficulty in recapturing the prosthetic heart valve device, should that be necessary. In some examples, a delivery system may be configured to stop at additional partial deployment configurations in order to enhance evaluation of a prosthetic heart valve device during implantation in a patient.

In some examples, a delivery system is configured such that a stop at the one or more partial deployment configurations is caused by a pathway switch from a first fluid pathway to a second fluid pathway. The delivery system is configured to cause the pathway switch using a stop pin having a first pin position which allows flow through a first fluid pathway, and having a second pin position which blocks flow through a first fluid pathway. In some examples, a delivery system is configured such that delivery of a pressurized fluid along a first fluid pathway drives a stop pin from a first pin position to a second pin position. When the stop pin fully, substantially, or partly achieves a second pin position (blocking the first fluid pathway), a delivery system is configured to direct flow through a second fluid pathway via a valve.

For example, the delivery system may define an entrance fluid pathway with a first fluid pathway and a second fluid pathway configured for fluid communication with an entrance fluid pathway. In some examples, a stop pin may be configured to allow flow from the entrance fluid pathway to a first fluid pathway in a first pin position, and to block flow from the entrance fluid pathway to a first fluid pathway in a second pin position. In some examples, a valve allowing flow to the second fluid pathway may be configured to open when a stop pin is in a second pin position. For example, blocking flow from the entrance fluid pathway to a first fluid pathway may cause an increase in the pressure of a fluid in an entrance fluid pathway, and a valve may be a relief valve configured to open and allow flow to a second fluid pathway when the pressure exceeds, reaches, or approaches a particular setpoint. In some examples, a delivery system is configured to generate a stop at a first partial deployment configuration based on a time required for a valve to open (e.g., for the relief valve to lift) once a stop pin achieves a second pin position.

In some examples, the delivery system is configured such that a clinician controls a duration of the stop as the delivery system transitions from a first fluid pathway to a second fluid pathway. For example, a clinician may control the supply of fluid delivered to a delivery system, and cease delivery as the delivery system transitions between fluid pathways. In some examples, ceasing the delivery may fully or partially stop or impede the delivery system's transition between fluid pathways, fully, substantially, or partly maintaining positions of a capsule housing and a prosthetic heart valve relative to each other or relative to one or more other reference markers. In some examples, a clinician may maintain a relatively static configuration between the capsule housing and a prosthetic heart valve device for as long as desired before recommencing supply of a pressurized fluid, withdrawing a capsule housing and a prosthetic heart valve device from the patient, or some other action.

In some examples, a delivery system may include a recapture fluid circuit configured to allow recapture of a prosthetic heart valve device using a capsule housing. In some examples, a recapture fluid circuit is configured to cause a capsule housing to fully, substantially, or partly re-sheathe a prosthetic heart valve device. In some examples, a delivery system is configured such that supply of a fluid via a first fluid pathway and/or a second fluid pathway causes a capsule housing to move in a first direction (e.g., proximally) relative to a prosthetic heart valve device, and supply a fluid via a recapture fluid circuit causes a capsule housing to move in a direction fully, substantially, or partly opposite a first direction (e.g., distally) relative to a prosthetic heart valve device (e.g., to re-sheathe).

In some examples, a native mitral valve or other type of native or prosthetic valve can be accessed through a patient's vasculature in a percutaneous manner for delivery of valve replacement devices. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a trans-apical approach. Depending on the approach, the interventional tools and supporting catheter(s) may be advanced to the heart intravascularly and positioned adjacent the target cardiac valve in a variety of manners, as known to a person having ordinary skill in the art.

Expanding valve replacement devices may be delivered through a patient's vasculature in a percutaneous manner utilizing appropriately configured delivery systems. FIG. 1 is an isometric view of one such example delivery system 100 for delivering a prosthetic heart valve device. Delivery system 100 may include a handle 101, a delivery catheter 102 having an elongated catheter body 103, and a delivery capsule 106. The catheter body 103 may include a proximal portion 103*a* and a distal portion 103*b* carrying the delivery capsule 106. The delivery capsule 106 may contain a medical device such as prosthetic heart valve device 110 (shown schematically in broken lines).

A control unit 112 coupled to the proximal portion 103*a* of catheter body 103 may provide steering capability (e.g., 360 degree rotation of the delivery capsule 106, 180 degree rotation of the delivery capsule 106, 3-axis steering, 2-axis steering, etc.) used to deliver the delivery capsule 106 to a target site (e.g., to a native mitral valve) and deploy the prosthetic heart valve device at the target site. The delivery catheter 102 can be configured to travel over a guidewire 114, which can be used to guide the delivery capsule 106 into, for example, a native heart valve. Delivery system 100 may also include a fluid assembly 116 configured to supply fluid to and receive fluid from the delivery catheter 102 and/or other components within delivery system 100 to, for example, cause the delivery capsule 106 to deploy and/or recapture the prosthetic heart valve device 110. The fluid assembly 116 may include a fluid source 118 and one or more fluid lines such as fluid line 120 fluidically coupling the fluid source 118 to the delivery catheter 102 and/or other components within delivery system 100. The fluid source 118 may contain a flowable substance (e.g., water, saline, etc.) in one or more reservoirs.

The control unit 112 can include a control assembly 122 and a steering mechanism 124. For example, the control assembly 122 can include rotational elements, such as a knob, that can be rotated to rotate the delivery capsule 106 about its longitudinal axis 126. The control assembly 122 can also include features that allow a clinician to control deployment mechanisms of the delivery capsule 106 and/or the fluid assembly 116. For example, the control assembly 122 can include buttons, levers, and/or other actuators that initiate unsheathing and/or resheathing the prosthetic heart valve device 110. The steering mechanism 124 can be used to steer the delivery catheter 102 through the anatomy by bending the distal portion 103b of the catheter body 103 about a transverse axis. In other embodiments, the control unit 112 may include additional and/or different features that facilitate delivering the prosthetic heart valve device 110 to the target site.

The delivery capsule 106 may include a capsule housing 128 configured to carry the prosthetic heart valve device 110 in a containment configuration and, optionally, an end cap 130 that extends distally from the capsule housing 128 and encloses the prosthetic heart valve device 110 in the capsule housing 128. The end cap 130 may have an opening 131 at its distal end through which the guidewire 114 can be threaded to allow for guidewire delivery to the target site. As shown in FIG. 1, the end cap 130 can also have an atraumatic shape (e.g., a partially spherical shape, a frusto-conical shape, blunt configuration, rounded configuration, etc.) to facilitate atraumatic delivery of the delivery capsule 106 to the target site. In certain embodiments, the end cap 130 can also house a portion of the prosthetic heart valve device 110.

In FIG. 1, delivery system 100 is illustrated in a containment configuration. In the containment configuration, delivery system 100 maintains capsule housing 128 in a position whereby capsule housing 128 (and optionally end cap 130) substantially surrounds prosthetic heart valve device 110, such that capsule housing 128 constrains prosthetic heart valve device 110 from radially expanding (e.g., expanding perpendicular to longitudinal axis 126). Delivery system 100 is configured to cause prosthetic heat valve device 110 to deploy from within delivery capsule 106 by causing capsule housing 128 to move proximally (e.g., in the direction P) relative to prosthetic heart valve device 110, such that capsule housing 128 constrains a portion of prosthetic heart valve device 110 from radially expanding while allowing the remaining portion of the prosthetic heart valve to radially expand without constraint by capsule housing 128 (e.g., a partial deployment configuration). Delivery system 100 is configured to further withdraw capsule housing 128 proximally (relative to relative to prosthetic heart valve device 110) until capsule housing 128 provides substantially no constraint on the radial expansion of prosthetic heart valve device 110. In this manner, delivery system 100 is configured to cause prosthetic heat valve device 110 to deploy from within delivery capsule 106 when delivery capsule 106 is positioned adjacent the target cardiac valve. In some examples, delivery system 100 is configured to cause capsule housing 128 to move distally relative to prosthetic heart valve device 110 to at least partially resheathe prosthetic heart valve 110, if desired.

Figure 2B:
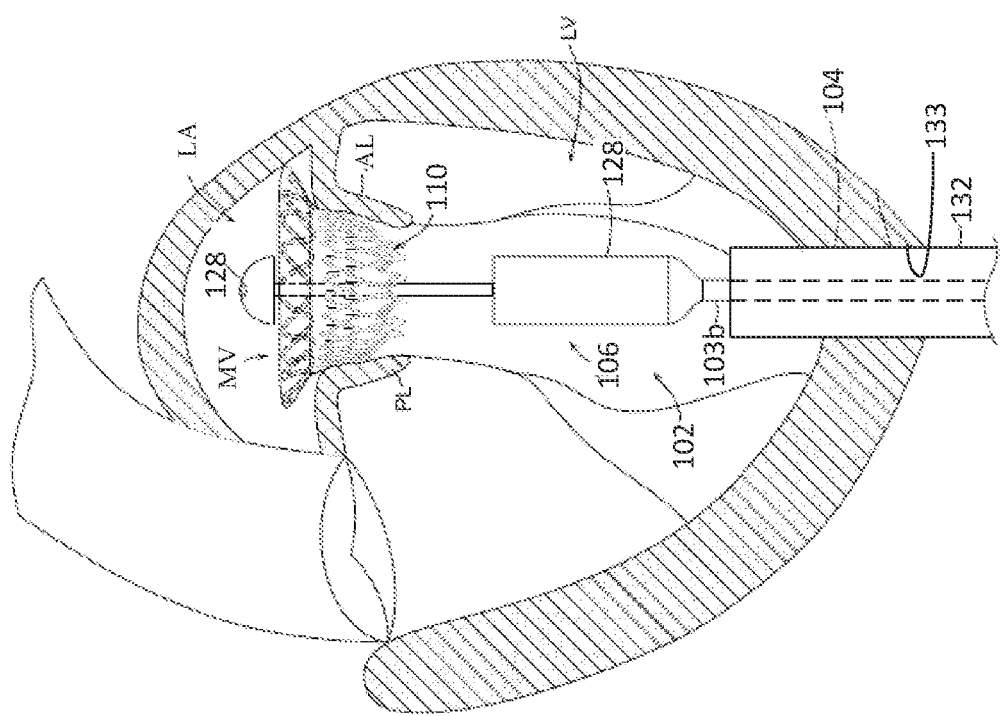
FIG. 2B is a schematic illustration of the distal portion of the system of FIG. 2A in a deployment configuration and a deployed example prosthetic heart valve device.
Figure 2A:
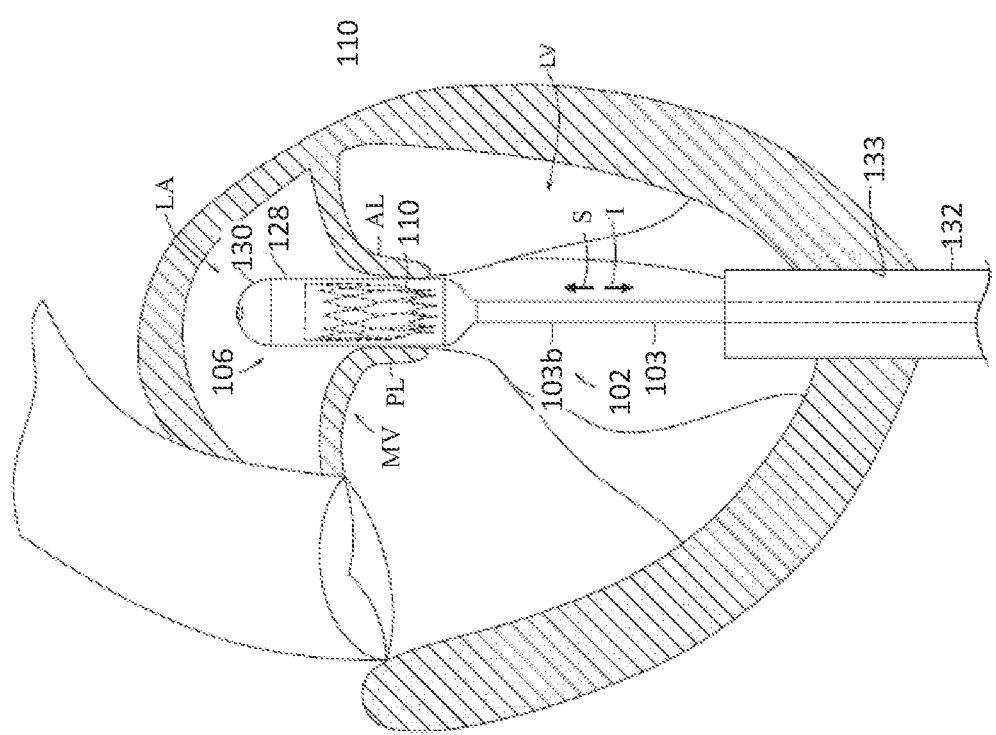
FIG. 2A is a schematic illustration of a distal portion of a delivery system positioned in a native mitral valve of a heart using a trans-apical delivery approach.

FIG. 2A illustrates delivery system 100 (e.g., delivery catheter 102) maintaining prosthetic heart valve device 110 and capsule housing 128 in the containment configuration, where capsule housing 128 constrains prosthetic heart valve device against radial expansion. FIG. 2B illustrates delivery system 100 (e.g., delivery catheter 102) maintaining prosthetic heart valve device 110 and capsule housing 128 in the deployment configuration, where capsule housing 128 provides substantially no constraint on the radial expansion of prosthetic heart valve device 110. For the purpose of illustration, FIG. 2A and FIG. 2B illustrate a portion of delivery system 100 positioning the prosthetic heart valve device 110 in a native mitral valve of a heart using a trans-apical delivery approach. Other approaches may be utilized, such as a trans-septal delivery approach. Referring to FIG. 2A, a guide catheter 132 is positioned in a trans-apical opening 133 to provide access to the left ventricle LV, with the delivery catheter 102 extending through the guide catheter 132 such that the distal portion 103b of the catheter body 103 projects beyond the distal end of the guide catheter 132. The delivery capsule 106 may then be positioned between a posterior leaflet PL and an anterior leaflet AL of a mitral valve MV. Using the control unit 112 (FIG. 1), the catheter body 103 can be moved in the superior direction (as indicated by arrow S), the inferior direction (as indicated by arrow I), and/or rotated along the longitudinal axis of the catheter body 103 to position the delivery capsule 106 at a desired location and orientation within the opening of the mitral valve MV.

At the target location, the delivery capsule 106 can be driven from the containment configuration (FIG. 2A) towards the deployment configuration (FIG. 2B) to fully deploy the prosthetic heart valve device 110 from the delivery capsule 106. Referring to FIG. 2B, in trans-apical delivery approaches, an example device such as prosthetic heart valve device 110 may be deployed from the delivery capsule 106 by drawing the capsule housing 128 proximally (e.g., further into the left ventricle LV) and, optionally, moving the end cap 130 distally (e.g., further into the left atrium LA). As the prosthetic heart valve device 110 exits the capsule housing 128, the prosthetic heart valve device 110 may expand to secure the prosthetic heart valve device 110 in the mitral valve MV.

The examples provided are described herein with reference to devices, systems, and methods for loading and deploying prosthetic heart valve devices to a native mitral valve. However, other applications and other embodiments in addition to those described herein are within the scope of the present technology. For example, at least some embodiments of the present technology may be useful for delivering and deploying prosthetics to other native valves, such as the tricuspid valve or the aortic valve.

Delivery system 100 is configured to transition from a containment configuration (FIG. 2A), to one or more partial deployment configurations, and to the deployment configuration (FIG. 2B). Delivery system 100 may be configured to be hydraulically driven by a pressurized fluid and transition among the configurations using a first fluid pathway and a second fluid pathway. Delivery system 100 is configured to at least momentarily stop the relative motion between capsule housing 128 and prosthetic heart valve device 110 when routing of the pressurized fluid switches from the first fluid pathway to the second fluid pathway (and vice-versa).

Figure 3:
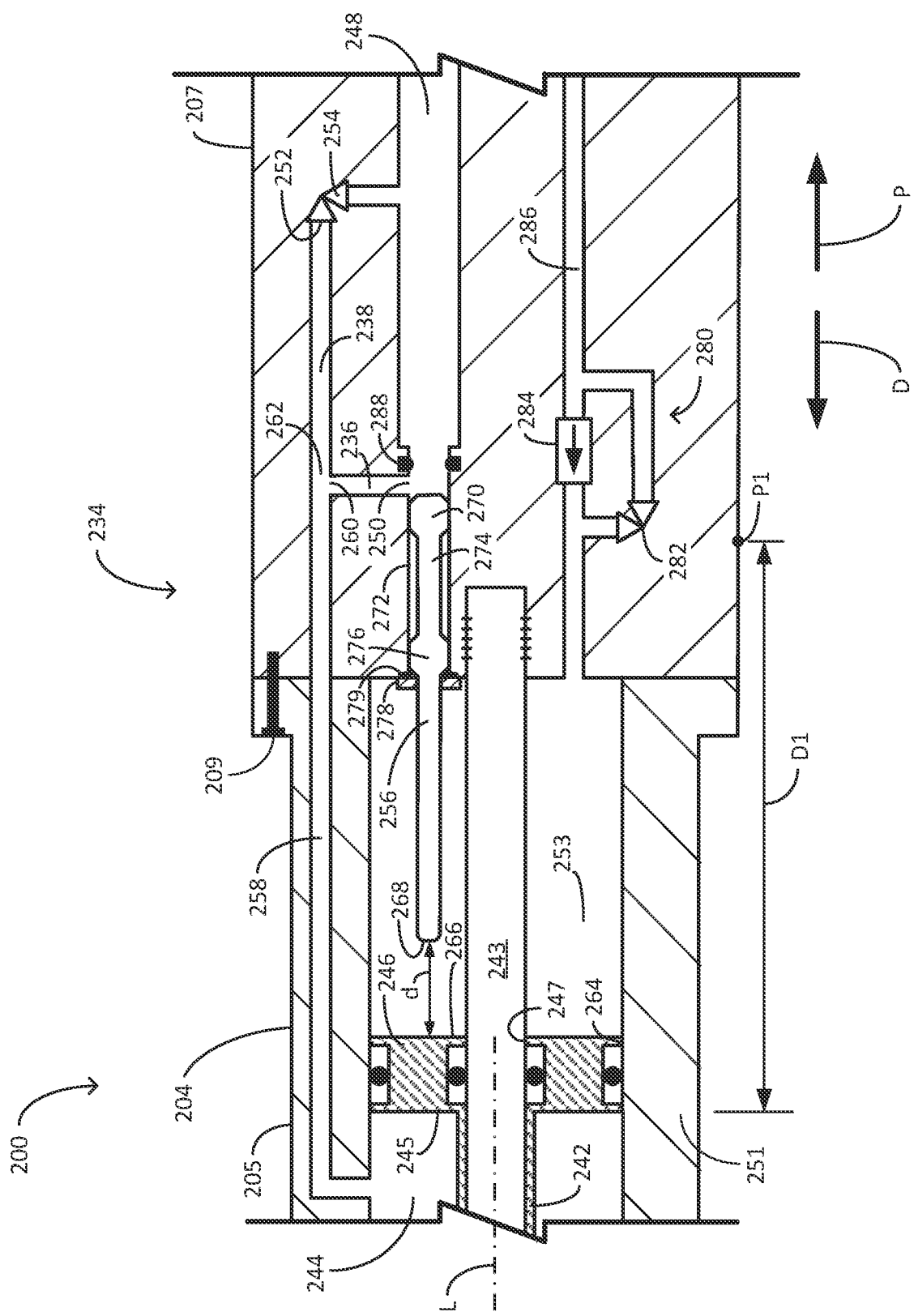
FIG. 3 is a cross-sectional illustration of an example delivery system.

FIG. 3 is a schematic illustration of a portion of a delivery system 200 ("delivery system 200") including system body 204. FIG. 3 depicts delivery system 200 configured to use a first fluid pathway to drive delivery system 200 from a containment configuration to a partial deployment configuration (e.g., a first partial deployment configuration). Delivery system 200 and/or system body 204 may be examples of a portion of delivery system 100. In some examples, delivery system 200 and/or system body 204 are portions of handle 101 of delivery system 100. In some examples, delivery system 200 and/or system body 204 are portions of catheter 103 of delivery system 100. In some examples, delivery system 200 and/or system body 204 are portions of both handle 101 and delivery catheter 103 of delivery system 100. In FIG. 3, system body 204 is illustrated as a cross-section with a cutting plane taken parallel to the page.

Delivery system 200 is configured to be hydraulically driven between a containment configuration for holding a prosthetic heart valve device (e.g., prosthetic heart valve device 110) and a deployment configuration for at least partially deploying the prosthetic heart valve device. System body 204 includes a distal portion 205 and a proximal portion 207, and defines a longitudinal axis L intersecting distal portion 205 and proximal portion 207. In some examples, distal portion 205 and proximal portion 207 are separable parts of system body 204 configured for attachment to each other using, for example, fastener 209. In some examples, distal portion 205 and proximal portion are substantially inseparable and define portions of a unified body comprising system body 204.

Delivery system 200 defines a hydraulic circuit 234 including a first fluid pathway 236 and a second fluid pathway 238. Delivery system 200 may be configured to use first fluid pathway 236 and second fluid pathway 238 to cause relative motion between a capsule housing (e.g., capsule housing 128 (FIG. 1, 2)) and a prosthetic heart valve device (e.g., prosthetic heart valve device 110 (FIG. 1, 2)). In some examples, delivery system 200 is configured to use first fluid pathway 236 and second fluid pathway 238 to drive movement of the capsule housing and the prosthetic heart valve device from one of a containment configuration, a first partial deployment position, a second partial deployment configuration, or a fully deployed position to another of the containment configuration, the first partial deployment position, the second partial deployment configuration, or the fully deployed position. In some examples, delivery system 200 is configured to use first fluid pathway 236 and second fluid pathway 238 to cause relative motion between an outer shaft 242 relative to system body 204. Outer shaft 242 may be mechanically coupled with capsule housing 128 or prosthetic heart valve device 110. In the example of FIG. 3, outer shaft 242 is depicted as a cross-section with a cutting plane parallel to the page. Delivery system 200 may be configured to receive a fluid from fluid source 118 (FIG. 1) and route the fluid through hydraulic circuit 234 in order to cause relative motion between the capsule housing and the prosthetic heart valve device.

In some examples, outer shaft 242 is configured for mechanical coupling with capsule housing 128 (FIG. 1, 2). Outer shaft 242 may be configured such that, when mechanically coupled to capsule housing 128, translation of outer shaft 242 proximally (e.g., in the proximal direction P) relative to system body 204 causes capsule housing 128 to translate proximally relative to prosthetic heart valve device 110. In some examples, outer shaft 242 slidably translates over an inner shaft 243 configured to remain stable relative to system body 204 when outer shaft 242 translates relative to system body 204. In some examples, inner shaft 243 is configured for mechanical coupling with end cap 130 of delivery capsule 106 (FIG. 1), such that when outer shaft 242 translates proximally relative to inner shaft 243, capsule housing 128 translates proximally relative to end cap 130. Hence, delivery system 200 may be configured to cause delivery capsule 106 to unsheathe the prosthetic heart valve device 110.

Delivery system 200 is configured to route a deployment fluid through first fluid pathway 236 or second fluid pathway 238 in order to cause outer shaft 242 to move in the proximal direction P relative to system body 204. First fluid pathway 236 and second fluid pathway 238 are each configured to provide the deployment fluid to a first chamber 244, with first chamber 244 configured to cause translation of outer shaft 242 in the proximal direction P. For example, first chamber 244 may be configured to direct a pressure of the deployment fluid against a first piston face 245 of a piston 246, causing piston 246 to translate in the proximal direction P. Piston 246 may be mechanically coupled to outer shaft 242, such that the movement of piston 246 in the proximal direction P causes movement of outer shaft 242 in the proximal direction P. In the example of FIG. 3, piston 246 is depicted as a cross-section with a cutting plane parallel to the page.

In some examples, piston 246 includes an inner peripheral surface 247 defining a central passage passing longitudinally through piston 246 and outer shaft 242. Inner shaft 243 may be configured to insert into the central passage defined by inner peripheral surface 247, such that piston 246 and outer shaft 242 substantially surround inner shaft 243. In some examples, the central passage defined by inner peripheral surface 247 substantially surrounds longitudinal axis L. In some examples, inner peripheral surface 247 is configured to slidably translate over inner shaft 243 when piston 246 translates within first chamber 244 due to, for example, the pressure of the deployment fluid acting on first piston face 245.

Delivery system 200 is configured to switch between using first fluid pathway 236 and using second fluid pathway 238 to deliver the deployment fluid to first chamber 244. First fluid pathway 236 and second fluid pathway 238 may be configured as substantially parallel fluid pathways for routing the deployment fluid to first chamber 244. For example, first fluid pathway 236 and second fluid pathway 238 may be configured for fluid communication with a fluid entrance pathway 248 configured to receive the deployment fluid. Delivery system 200 may define a first inlet 250 configured to establish fluid communication between fluid entrance pathway 248 and first fluid pathway 236. Delivery system 200 may define a second inlet 252 configured to establish fluid communication between fluid entrance pathway 248 and second fluid pathway 238. Delivery system 200 may be configured to route the deployment fluid from fluid entrance pathway 248 through first inlet 250 of first fluid pathway 236 and to first chamber 244, and may be configured to route the deployment fluid from fluid entrance pathway 248 through second inlet 252 of second fluid pathway 238 and to first chamber 244. In some examples, delivery system 200 is configured to selectively route the deployment fluid to first chamber 244 either through first inlet 250 and first fluid pathway 236 or through second inlet 252 and second fluid pathway 238.

Delivery system 200 includes a valve 254 which may fluidly isolate or fluidly connect second inlet 252 and fluid entrance pathway 248. Valve 254 may be, for example, a pressure relief valve configured to lift (e.g., open) and establish fluid communication between fluid entrance pathway 248 and second inlet 252 when a fluid pressure in fluid entrance pathway 248 exceeds a setpoint of valve 254. Delivery system 200 further includes a stop pin 256 configured to block flow through first fluid pathway 236 (e.g., to block flow from fluid entrance pathway 248 through first inlet 250). In some examples, stop pin 256 is configured to slidably translate (e.g., in the proximal direction P) within system body 204 to block through first fluid pathway 236. Stop pin 256 may be configured such that further translation in the proximal direction P re-establishes flow through first fluid pathway 236.

In some examples, delivery system 200 may be configured to define a deployment fluid conduit 258 in fluid communication with first chamber 244. Deployment fluid conduit 258 may additionally be in fluid communication with a first outlet 260 of first fluid pathway 236 and a second outlet 262 of second fluid pathway 238, such that first fluid pathway 236 and second fluid pathway 238 define parallel fluid paths between fluid entrance pathway 248 and deployment fluid conduit 258. In other examples, first outlet 260 and/or second outlet 262 are configured to provide a flow outlet directly into first chamber 244 without the use of a defined intermediate flow path such as deployment fluid conduit 258.

Delivery system 200 is configured to cause translation of outer shaft 242 using first fluid pathway 236 and second fluid pathway 238. Delivery system 200 is configured to switch between using first fluid pathway 236 and using second fluid pathway 238 to deliver the deployment fluid to first chamber 244, in order to cause the translation of outer shaft 242 in the proximal direction P. Delivery system 200 is configured to at least momentarily stop the translation of outer shaft 242 as delivery system 200 transitions between first flow pathway 236 and second flow pathway 238. In some examples, delivery system 200 is configured such that providing the deployment fluid to first chamber 244 via first fluid pathway 236 causes delivery system 200 to switch the flow path from first fluid pathway 236 to second fluid pathway 238. In some examples, delivery system 200 is configured such that providing the deployment fluid to first chamber 244 via second fluid pathway 238 causes delivery system 200 to switch the flow path from second fluid pathway 238 to first fluid pathway 236.

For example, FIG. 3 illustrates delivery system 200 in a containment configuration with piston 246 in a first piston location within system body 204. In the first piston location, piston 246 defines a first displacement D1 between a first piston face 245 and a point P1 on system body 204. In an example, first displacement D1 is substantially parallel to longitudinal axis L. Delivery system 200 may be configured such that, when piston 246 is in the first piston location, outer shaft 242 is positioned to maintain capsule housing 128 in a position whereby capsule housing 128 constrains prosthetic heart valve 110 from radially expanding. For example, in the first piston location, outer shaft 242 may be positioned to maintain capsule housing 128 and prosthetic heart valve device 110 in the relative positions depicted in FIG. 2A. In the containment configuration of delivery system 200 illustrated in FIG. 3, stop pin 256 is positioned within system body 204 to allow a flow of deployment fluid from fluid entrance pathway 248 through first fluid pathway 236 via first inlet 250. Valve 254 is in a closed position blocking flow from fluid entrance pathway 248 to second fluid pathway 238 via second inlet 252.

Fluid entrance pathway 248 is configured to receive a pressurized deployment fluid (e.g., from fluid source 118 via fluid line 120 (FIG. 1). In the containment configuration of FIG. 3, delivery system 200 is configured to route the pressurized fluid to first chamber 244 using fluid entrance pathway 248, first fluid pathway 236, and deployment fluid conduit 258. With valve 254 in the closed position, delivery system 200 blocks flow of the deployment fluid from fluid entrance pathway 248, through second inlet 252, and through second fluid pathway 238. Hence, in the containment configuration shown in FIG. 3, delivery system 200 is configured to provide a flow of a deployment fluid to first chamber 244 using first fluid pathway 236 while blocking a flow of the deployment fluid through second fluid pathway 238.

First chamber 244 may be configured to cause a pressure of the deployment fluid to act against first piston face 245 of piston 246. Piston 246 is configured to translate (e.g., in the proximal direction P) in response to the pressure of the deployment fluid acting on first piston face 245. Piston 246 may be configured to translate in a direction substantially parallel to longitudinal axis L. In some examples, first chamber 244 is defined by a first portion of a piston cylinder defined by a cylinder wall 251 of system body 204. Cylinder wall 251 may be configured to substantially surround an outer peripheral surface 264 of piston 246. In some examples, cylinder wall 251 defines a second chamber 253. Piston 246 may be configured to translate in a direction from first chamber 244 toward second chamber 253. Outer peripheral surface 264 may be configured to slidably translate over cylinder wall 251 when piston 246 translates within first chamber 244 due to, for example, the pressure of the deployment fluid acting on first piston face 245. Piston 246 may be configured to fluidly isolate first chamber 244 and second chamber 253.

Figure 4:
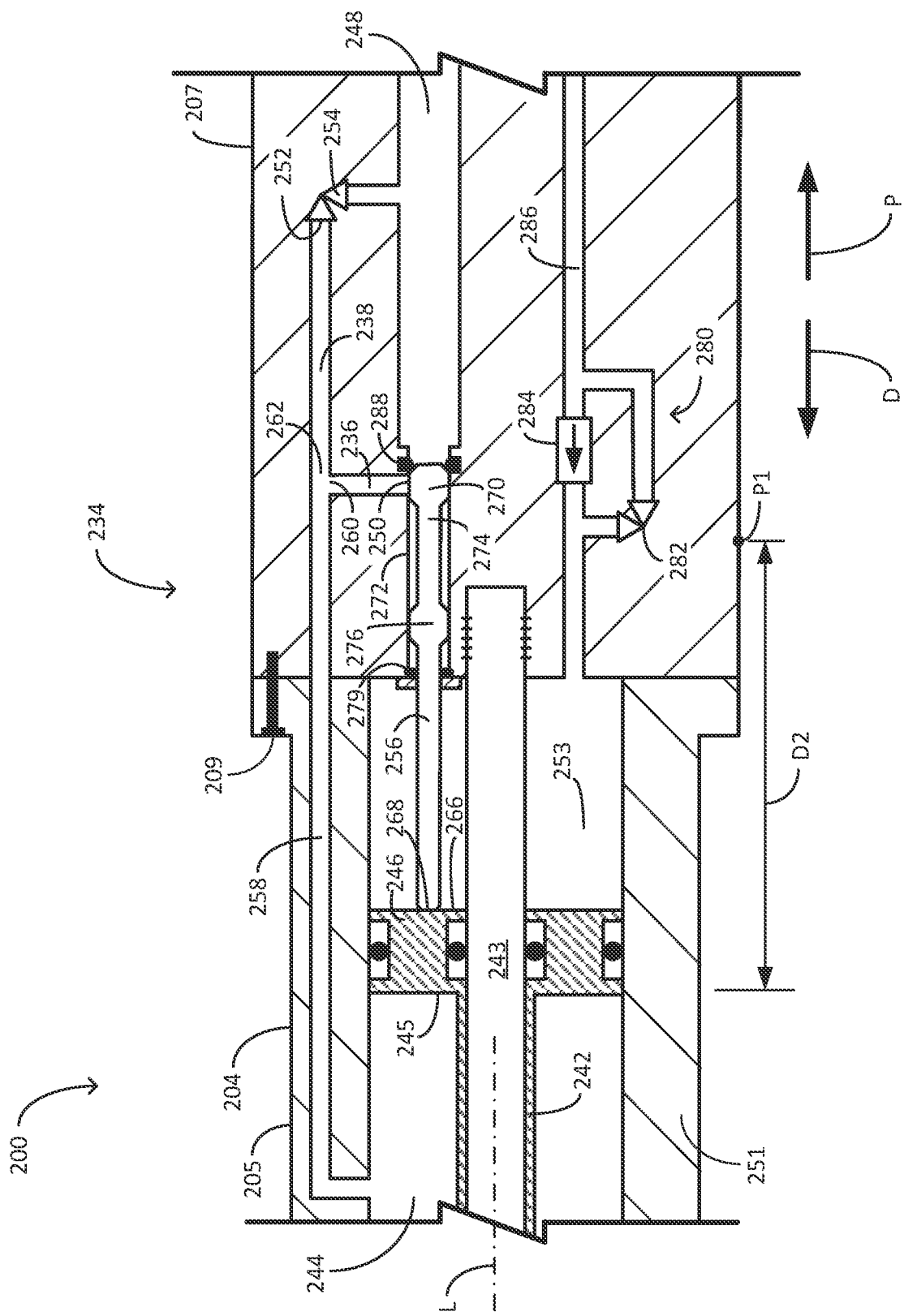
FIG. 4 is a cross-sectional illustration of the delivery system of FIG. 3 in an example configuration.

Further, in the containment configuration of FIG. 3, stop pin 256 is positioned within system body 204 to allow the flow of deployment fluid to first chamber 244 using first fluid pathway 236. Stop pin 256 may be configured to translate within delivery system 200 from a first pin position allowing flow through first fluid pathway 236 to a second pin position which blocks flow through first fluid pathway 236. For example, stop pin 256 may include a first land 270. Stop pin 256 may be configured within delivery system 200 to translate from a first pin position wherein first land 270 allows flow through first inlet 250 and first fluid pathway 236 (as depicted in FIG. 3) to a second pin position wherein first land 270 blocks flow through first inlet 250 and first fluid pathway 236 (as depicted in FIG. 4).

Stop pin 256 is configured to allow hydraulic delivery of a deployment fluid along first fluid pathway 236 in the first pin position and block hydraulic delivery of the deployment fluid flows along first fluid pathway 236 in the second pin position. In some examples, system body 204 defines a pin channel 272 (FIG. 3, 4) configured to guide stop pin 256 from the first pin position to the second pin position. Stop pin 256 may be configured to slidably translate within pin channel 272. In some examples, stop pin 256 is an elongate member having one or more sections (e.g., first land 270) configured to allow a fluid flow through first inlet 250 when stop pin 256 is in the first pin position and configured to block a fluid flow through first inlet 250 when stop pin 256 is in the second pin position. Stop pin 256 may define any cross-sectional profile (e.g., a profile perpendicular to longitudinal axis L). In example, stop pin 256 defines a circular or oval shaped cross-sectional profile. In some examples, stop pin 256 defines a rounded spool having at least land 270 protruding radially relative to a groove section 274 adjacent land 270. In some examples, stop pin 256 further includes a land 276 separated from land 270 by groove section 274. In an example, pin channel 272 is configured to maintain at least a distal end 268 of stop pin 256 ("stop pin distal end 268") within second chamber 253 when stop pin 256 is in the first pin position. In some examples, delivery system 200 is configured to limit translation of stop pin 256 in a distal direction (e.g., into second chamber 253). For example, delivery system 200 may include a flange 278 configured to limit distal travel of stop pin 256. In some examples, delivery system 200 is configured provide a seal around stop pin 256 to substantially prevent flow between fluid entrance pathway 248 and/or first fluid pathway 236 and second chamber 253 via pin channel 272. For example, delivery system 200 may include O-ring 279 around pin channel 272 and configured to provide the seal around stop pin 256.

Delivery system 200 is configured to drive stop pin 256 from the first pin position in which the deployment fluid flows along first fluid pathway 236 to the second pin position in which the deployment fluid is blocked from flowing along first fluid pathway 236. Delivery system 200 may be configured to drive stop pin 256 from the first pin position to the second pin position using a hydraulic delivery of deployment fluid through first fluid pathway 236 to first chamber 244. In an example, delivery system 200 drives piston 246 toward stop pin 256 as the pressure of the deployment fluid in first chamber 244 causes a translation of piston 246 toward stop pin 256. Delivery system 200 may be configured such that when piston 246 contacts a distal end 268 of stop pin 256 ("stop pin distal end 268"), continued translation of piston 246 toward stop pin 256 causes a translation of stop pin 256 from the first pin position to the second pin position. For example, piston 246 may include a second piston face 266 opposite first piston face 245 configured to translate stop pin 256. Second piston face 266 may be in fluid communication with second chamber 253.

In some examples, piston 246 is displaced from stop pin distal end 268 by a distance d when delivery system 200 is in the containment configuration, such that piston 246 is required to translate over the distance d before piston 246 (e.g., second piston face 266) contacts stop pin distal end 268. Configuring delivery catheter 202 to include the distance d may allow a reduction in the space footprint of hydraulic circuit 234 within delivery system 200. For example, including the distance d may reduce a required length of stop pin 256 within delivery system 200. In other examples, piston 246 (e.g., second piston face 266) is in contact with stop pin distal end 268 when delivery system 200 is in the containment configuration.

Delivery system 200 may include a recapture circuit 280 configured to substantially maintain a pressure of second chamber 253 within a particular range. Maintaining the pressure of second chamber 253 within the particular range may limit the pressure of a deployment fluid within first chamber 244 that must be supplied to affect movement of piston 246. For example, when second chamber 253 holds a fluid and piston 246 translates in the proximal direction P, piston 246 may compress the fluid within second chamber 253, causing a pressure in second chamber 253 to increase. In some examples, recapture circuit 280 includes a valve 282 configured to allow a fluid flow to exit second pressure chamber 253 when the pressure in second chamber 253 exceeds a setpoint pressure. In some examples, valve 282 is a relief valve configured to lift (e.g., fully or partially lift) when the pressure exceeds the setpoint pressure of valve 282. Valve 282 may be configured to have a closing pressure wherein valve 282 shuts (or is caused to shut) after lifting at the setpoint pressure. Thus, as piston 246 translates proximally, valve 282 may be configured to maintain a pressure in second chamber 253 within or close to a range bounded by the pressure setpoint and the closing pressure.

Recapture circuit 280 may be configured to increase the pressure in second chamber 253 in order to, for example, cause piston 246 to move in a direction opposite that caused by the deployment fluid supplied via first fluid pathway 236 and second fluid pathway 238. Causing piston 246 to move in the opposite direction (e.g., distally) may cause capsule housing 128 to move relative to prosthetic heart valve device 110 in the opposite direction, such that capsule housing 128 at least partially re-sheathes prosthetic heart valve device 110. In some examples, recapture circuit includes a valve 284 configured to allow a flow of fluid into second chamber 253 to cause the increased pressure. Valve 284 may be a check valve configured to allow the flow into second chamber 253 and substantially prevent a flow from exiting second chamber 253.

In some examples, recapture circuit 280 includes a recapture fluid pathway 286 in fluid communication with valve 282 and valve 284. Recapture fluid pathway 286 may be configured such that valve 282 (e.g., a relief valve) opens to provide a bypass around valve 284 (e.g., a check valve) when the pressure in second chamber 253 exceeds the pressure setpoint. In some examples, recapture circuit 280 may be configured such that valve 282 enables a fluid flow through a relief fluid pathway and valve 284 enables flow through a supply fluid pathway separate from the relief fluid pathway.

FIG. 4 illustrates delivery system 200 with piston 246 proximally displaced from the first piston location of FIG. 3 and having driven stop pin 256 from the first pin position to the second pin position. Delivery system 200 is configured such that stop pin 256 blocks flow of the deployment fluid through first fluid pathway 236. Delivery system 200 may cause the proximal displacement of piston 246 using a deployment fluid supplied via first fluid pathway 236. As piston 246 drives stop pin 256 to the second pin position, some portion of stop pin 256 (e.g., land 270) positions to block fluid flow through first inlet 250 and first fluid pathway 236. In some examples, delivery system 200 includes an O-ring 288 surrounding a periphery of pin channel 272 and/or fluid entrance pathway 248. Some portion of stop pin 256 (e.g., land 270) may be configured to seat against O-ring 288 when stop pin 256 is in the second pin position. With valve 254 in the closed position (e.g., with a pressure in fluid entrance pathway below a setpoint of valve 254) and stop pin 256 in the second pin position, fluid entrance pathway 248 is fluidly isolated from first chamber 244, and translation of piston 246 and outer shaft 242 substantially ceases. Correspondingly, when outer shaft 242 is mechanically coupled to capsule housing 128 (FIG. 1, 2), motion of capsule housing 128 relative to prosthetic heart valve device 110 substantially ceases.

Additionally, as piston 246 drives stop pin 256 to the second pin position, a pressure in second chamber 253 may increase (e.g., due to compression of a fluid in second chamber 253). Valve 282 may open to allow a flow from second chamber 253 when the pressure reaches a setpoint pressure, and may close when the pressure falls to a closing pressure. Hence, valve 282 may maintain the pressure within second chamber 253 in a range fully or approximately bounded by the setpoint pressure and the closing pressure as piston 246 drives stop pin 256 to the second pin position. In some examples, valve 282 includes a setpoint pressure adjustment mechanism (e.g., an adjustment screw) configured to adjust the setpoint pressure of valve 282. The setpoint adjustment mechanism of valve 282 may be utilized to increase or decrease the range fully or approximately bounded by the setpoint pressure and the closing pressure of valve 282.

In some examples, piston 246 establishes a second piston location within delivery system 200 when stop pin 256 is in the second pin position. In the second piston location, piston 246 defines a second displacement D2 between first piston face 245 and point P1 on system body 204, with the second displacement D2 having a magnitude different from the first displacement D1 of the first piston location (FIG. 3). In some examples, the point P1 is proximal to first piston face 245, and the second displacement D2 is less than the first displacement D1.

With stop pin 256 in the second pin position, delivery system 200 is configured to maintain piston 246 in a substantially static position relative to system body 204 until valve 254 opens to allow fluid flow from fluid entrance pathway 248 to second fluid pathway 238. For example, when valve 254 is a relief valve having a setpoint pressure, delivery system 200 is configured to maintain piston 246 in the substantially static position until a pressure in fluid entrance pathway 248 exceeds the setpoint pressure of valve 254. Hence, when a clinician controls the pressure within fluid entrance pathway 248 (e.g., using fluid source 118 and fluid line 120 (FIG. 1)), the clinician may cause delivery system 200 to substantially maintain piston 246 in the static position (and maintain capsule housing 128 static relative to prosthetic heart valve device 110 (FIG. 1, 2)) for as long a period as desired.

Further, because delivery system 200 is configured to substantially maintain the static position until the pressure in fluid entrance pathway 248 increases to the pressure setpoint of valve 254, delivery system 200 is configured to at least momentarily stop the translation of piston 246 when stop pin 256 drives to the second pin position. In an example, delivery system 200 is configured such that a pressure in first chamber 244 required to cause translation of piston 246 is less than the setpoint pressure of valve 254. In some examples, valve 254 includes a setpoint pressure adjustment mechanism (e.g., an adjustment screw) configured to adjust the setpoint pressure of valve 254. The setpoint adjustment mechanism of valve 254 may be utilized to lengthen or shorten the momentary stop when stop pin 256 drives to the second pin position.

In some examples, delivery system 200 establishes a first partial deployment configuration when stop pin 256 achieves the second pin position. Delivery system 200 may be configured such that, in the first partial deployment configuration, outer shaft 242 establishes capsule housing 128 relative to prosthetic heart valve device 110 such that capsule housing 128 constrains at least a portion of prosthetic heart valve device 110 (e.g., a proximal portion) from radially expanding. In some examples, outer shaft 242 establishes capsule housing 128 relative to prosthetic heart valve device 110 such that capsule housing 128 at surrounds the portion of prosthetic heart valve device 110 (e.g., the proximal portion). In some examples, the first partial deployment configuration of delivery catheter 202 may be configured to limit a radial expansion of the partially unsheathed prosthetic heart valve such that the prosthetic heart valve device may be repositioned relative to a target site (e.g., to a native mitral valve).

Delivery system 200 is configured such that when stop pin 256 is in the second pin position, the deployment fluid is directed via a valve through second fluid pathway 238. Directing the deployment fluid through second fluid pathway 238 may re-initiate proximal translation of piston 246. For example, with delivery system 200 configured as illustrated in FIG. 4 (e.g., with stop pin 256 in the second pin position and valve 254 in the closed position), proximal translation of piston 246 may be re-initiated by increasing a pressure of the deployment fluid within fluid entrance pathway 248. In an example, the pressure within fluid entrance pathway 248 is increased using fluid source 118 and fluid line 120 (FIG. 1). When the pressure in fluid entrance pathway 248 increases to or above the setpoint pressure of valve 254, valve 254 opens to supply deployment fluid to first chamber 244 via second inlet 252, second fluid pathway 238, and deployment fluid conduit 258. As before, first chamber 244 is configured to cause translation of piston 246 using the pressure of the deployment fluid. In some examples, first chamber 244 is configured to direct a pressure of the deployment fluid against first piston face 245 of a piston 246, causing translation of piston 246 in the proximal direction P.

FIGS. 10A-10D schematically illustrates a valve 400 configured to open when a pressure within fluid entrance pathway 248 is increased above a setpoint pressure. FIG. 10A illustrates valve 400 is in closed position while FIG. 10B illustrates valve 400 in an open position. FIG. 10C and FIG. 10D are cross-sections of FIG. 10A and FIG. 10B respectively, with a cutting plane taken parallel to the page. Valve 400 may be an example of valve 254 and valve 282.

Valve 400 includes an upper valve body 402 and a lower valve body 404. Valve 400 is configured such that upper valve body 402 and lower valve body 404 are substantially stationary with respect to each other. For example, upper valve body 402 may be attached to lower valve body 404. Valve 400 further includes valve stem 406 and valve seat 408. Valve stem 406 is configured such that a translation of valve stem 406 causes a translation of valve seat 408. Valve 400 may include a reference force element 410 configured to resist a translation of valve stem 406 in the opening direction O. Reference force element 410 may be configured to drive valve stem 406 in a closing direction. For example, reference force element may be spring configured such that translation of valve stem 406 in the opening direction causes compression of the spring (resisting translation of valve stem 406 in the opening direction) and translation of valve stem 406 in the closing direction causes an expansion of the compressed spring (driving translation of valve stem 406 in the closing direction). Valve 400 (e.g., upper valve body 402) further defines a valve inlet 412 and a valve outlet 414. Valve 400 (e.g., upper valve body 404) is configured to provide a flow path from valve inlet 412 to valve outlet 414 based on the position of valve stem 406 and valve seat 408.

Valve 400 may be an example of valve 254. Valve 400 may be configured within delivery system 200 such that valve seat 408 and valve inlet 412 are in fluid communication with fluid entrance pathway 248 and valve outlet 414 is in fluid communication with second inlet 252. With valve 400 in a closed position (FIGS. 10A and 10C), valve 400 is configured such that valve stem 406 and valve seat 408 fluidly isolate valve inlet 412 and valve outlet 414 (fluidly isolating fluid entrance pathway 248 and second inlet 252). Valve 400 may be configured within delivery system 200 such that increasing pressure within fluid entrance pathway 248 increases a pressure on valve seat 408, tending to cause valve seat 408 and valve stem 406 to move in the opening direction. When the pressure the pressure on valve seat 408 (e.g., the pressure in fluid entrance pathway 248) sufficiently increases to overcome the resistance of reference force element 410, valve stem 406 and valve seat 408 may move to an open position (FIGS. 10B and 10D), establishing fluid communication from valve inlet 412 to valve outlet 414 (e.g., between fluid entrance pathway 248 and second fluid pathway 238 via second inlet 252). A decrease in pressure on valve seat 408 below the pressure setpoint of valve 400 may cause reference force element 410 to drive valve stem 406 and valve seat 408 back toward the closed position (FIGS. 10A and 10C).

Hence, when valve stop pin 256 is in the second pin position (FIG. 4), pressure in fluid entrance pathway 248 may be increased until a pressure on valve seat 408 exceeds the setpoint pressure of valve 400, causing valve 400 to open and allow flow through second fluid pathway 238. Delivery system 200 may be configured such that delivery of a deployment fluid via second fluid pathway 238 causes proximal movement of piston 246 and stop pin 256. The hydraulic delivery via second fluid pathway 238 may cause stop pin 256 to move to the third pin position wherein the deployment fluid may flow through first fluid pathway 236. Allowing flow through first fluid pathway 236 may decrease a fluid pressure within fluid entrance pathway 248, causing reference force element 410 to drive valve stem 406 and valve seat 408 to the closed position (e.g., blocking flow from fluid entrance pathway 248 to second inlet 252.

In some examples, a setpoint pressure of valve 400 may be adjusted using reference force adjustor 416. Delivery system 200 may be configured such that reference force adjustor 416 is accessible from an exterior of system body 204, such that the pressure within fluid entrance pathway 248 required to open valve 400 is adjustable. Thus, reference force adjustor 416 may be utilized to control the amount of pressure increase within fluid entrance pathway 248 required to be supplied by fluid source 118 (FIG. 1) in order to re-initiate movement of piston 246 (e.g. re-initiate relative movement between capsule 106 and prosthetic heart valve device 110).

Valve 400 may be an example of valve 282 of recapture circuit 280. Valve 400 may be configured within delivery system 200 such that valve seat 408 and valve inlet 412 are in fluid communication with second chamber 253 and valve outlet 414 is in fluid communication with recapture fluid pathway 286. With valve 400 may be configured to block flow from second chamber 253 to recapture fluid pathway when valve 400 is in a closed position (FIGS. 10A and 10C). Valve 400 may be configured within delivery system 200 such that increasing pressure within second chamber 253 increases a pressure on valve seat 408, tending to cause valve seat 408 and valve stem 406 to move in the opening direction. When the pressure the pressure on valve seat 408 (e.g., the pressure in second chamber 253) sufficiently increases (e.g., due to proximal movement of piston 246) to overcome the resistance of reference force element 410, valve stem 406 and valve seat 408 may move to an open position (FIGS. 10B and 10D), establishing fluid communication from valve inlet 412 to valve outlet 414 (e.g., between second chamber 253 and recapture fluid circuit 280). A decrease in pressure within second chamber 253 may cause reference force element 410 to drive valve stem 406 and valve seat 408 back toward the closed position (FIGS. 10A and 10C). Delivery system 200 may be configured such that a reference force adjustor (e.g., reference force adjustor 416) of valve 282 is accessible from an exterior of system body 204. Hence, recapture circuit 280 may be configured to maintain a pressure or pressure range of second chamber 253.

Hydraulic circuit 234 is configured to drive stop pin 256 from the second pin position (FIG. 4) to the third pin position (FIG. 5) when the deployment fluid is directed via valve 254 through second flow pathway 238. When stop pin 256 is in the third pin position, hydraulic circuit 234 is configured to direct the deployment fluid along first fluid pathway 236. For example, and with reference to FIG. 4, translation of piston 246 causes a translation of stop pin 256 and drives stop pin 256 from the second pin position to a third pin position. Stop pin 256 is configured to allow a flow of deployment fluid through first fluid pathway 236 in the third pin position. For example, translation of piston 246 may cause a proximal translation of stop pin 256, causing stop pin 256 to translate from the second pin position wherein land 270 blocks flow through first inlet 250 and first fluid pathway 236 to a third pin position wherein groove section 274 allows flow through first inlet 250 and first fluid pathway 236. Some portion of stop pin 256 (e.g., land 270) may be configured to pass through an O-ring hole defined by an inner diameter of O-ring 288 when stop pin 256 translates from the second pin position to the third pin position. In some examples, land 270 is proximal to O-ring 288 when stop pin 256 is in the third pin position. In some examples, second land 276 is distal to O-ring 288 when stop pin 256 is in the third pin position.

Figure 5:
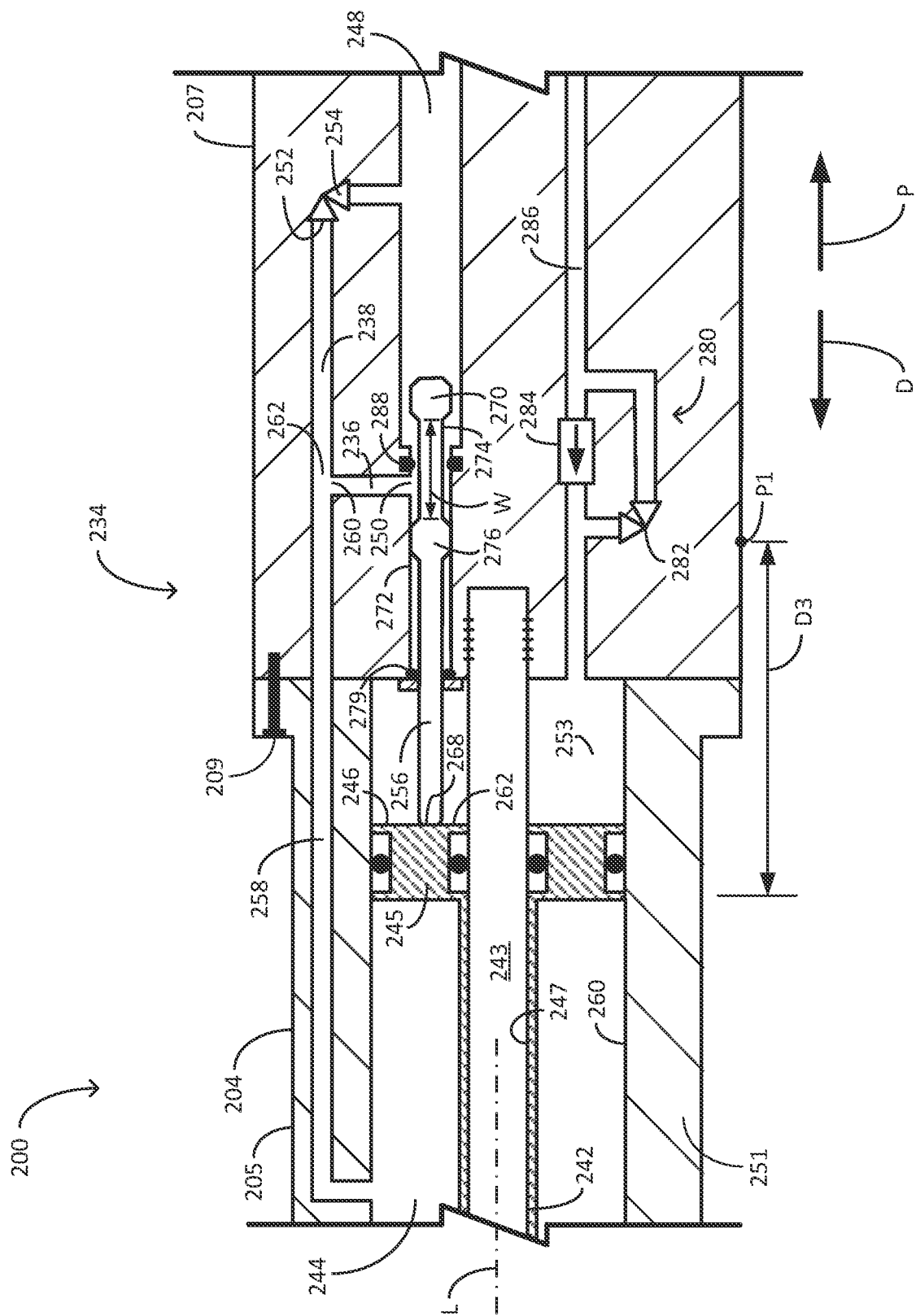
FIG. 5 is a cross-sectional illustration of the delivery system of FIG. 3 in another example configuration.

FIG. 5 illustrates delivery system 200 with piston 246 proximally displaced from the second piston location of FIG. 4 and having driven stop pin 256 from the second pin position to the third pin position. As piston 246 drives stop pin 256 to the third pin position, some portion of stop pin 256 (e.g., groove section 274) positions to allow flow through first inlet 250 and first fluid pathway 236. Delivery system 200 is configured to cause a decrease in the pressure in fluid entrance pathway 248 when stop pin 256 positions in the third pin position. For example, delivery system 200 may be configured such that a flow resistance from fluid entrance pathway 248 to first outlet 260 is less than a flow resistance from fluid entrance pathway 248 to second outlet 262 when valve 254 is open and stop pin 256 is in the third pin position. Valve 254 is configured to close when the pressure in fluid entrance pathway 248 is below the closing pressure of valve 254. With valve 254 in the closed position and stop pin 256 in the third pin position, delivery system 200 is configured to provide a flow of the deployment fluid through the first fluid pathway (e.g., through first inlet 250, first fluid pathway 236, and deployment fluid conduit 258) to first chamber 244. As before, delivery system 200 is configured to translate piston 246 (e.g., in the proximal direction P) using a pressure of a deployment fluid in first chamber 244. Delivery system 200 may be configured to cause a translation of stop pin 256 using the translation of piston 246.

In some examples, piston 246 assumes (e.g., translates through, or momentarily establishes) a third piston location within delivery system 200 when stop pin 256 is in the third pin position. In the third piston location, piston 246 defines a third displacement D3 between first piston face 245 and point P1 on system body 204, with the third displacement D3 having a magnitude different from the first displacement D1 of the first piston location (FIG. 3) and/or the second displacement D2 of the second piston location (FIG. 4). In some examples, the point P1 is proximal to first piston face 245, and the third displacement D3 is less than the second displacement D2.

Stop pin 256 may be configured to substantially remain in the third pin position while translating (e.g., in the proximal direction P) over some range. For example, stop pin 256 may substantially remain in the third pin position based on a width W of groove section 274. The width W of groove section 274 may extend over any length of stop pin 256. In some examples, the width W of groove section 274 extends from first land 270 to second land 276. In some examples, the width W of groove section 274 may extend from first land 270 to stop pin distal end 268. Stop pin 256 may have any number of lands and any number of groove sections extending between neighboring lands. In some examples, stop pin 256 includes at least first land 270 and second land 276, and the width W defines a displacement of piston 246 required to transition delivery system 200 from a first partial deployment configuration (FIG. 3) to a second partial deployment configuration.

With stop pin 256 in the third pin position, continued translation of piston 246 causes a translation of stop pin 256 and drives stop pin 256 from the third pin position to a fourth pin position. Stop pin 256 is configured to block the flow of deployment fluid through first fluid pathway 236 in the fourth pin position. In some examples, stop pin 256 includes second land 276. Stop pin 256 may be configured within delivery system 200 to translate from the third pin position wherein groove section 274 allows flow through first inlet 250 and first fluid pathway 236 (as depicted in FIG. 5) to the fourth pin position wherein second land 276 blocks flow through first inlet 250 and first fluid pathway 236 (as depicted in FIG. 6).

Figure 6:
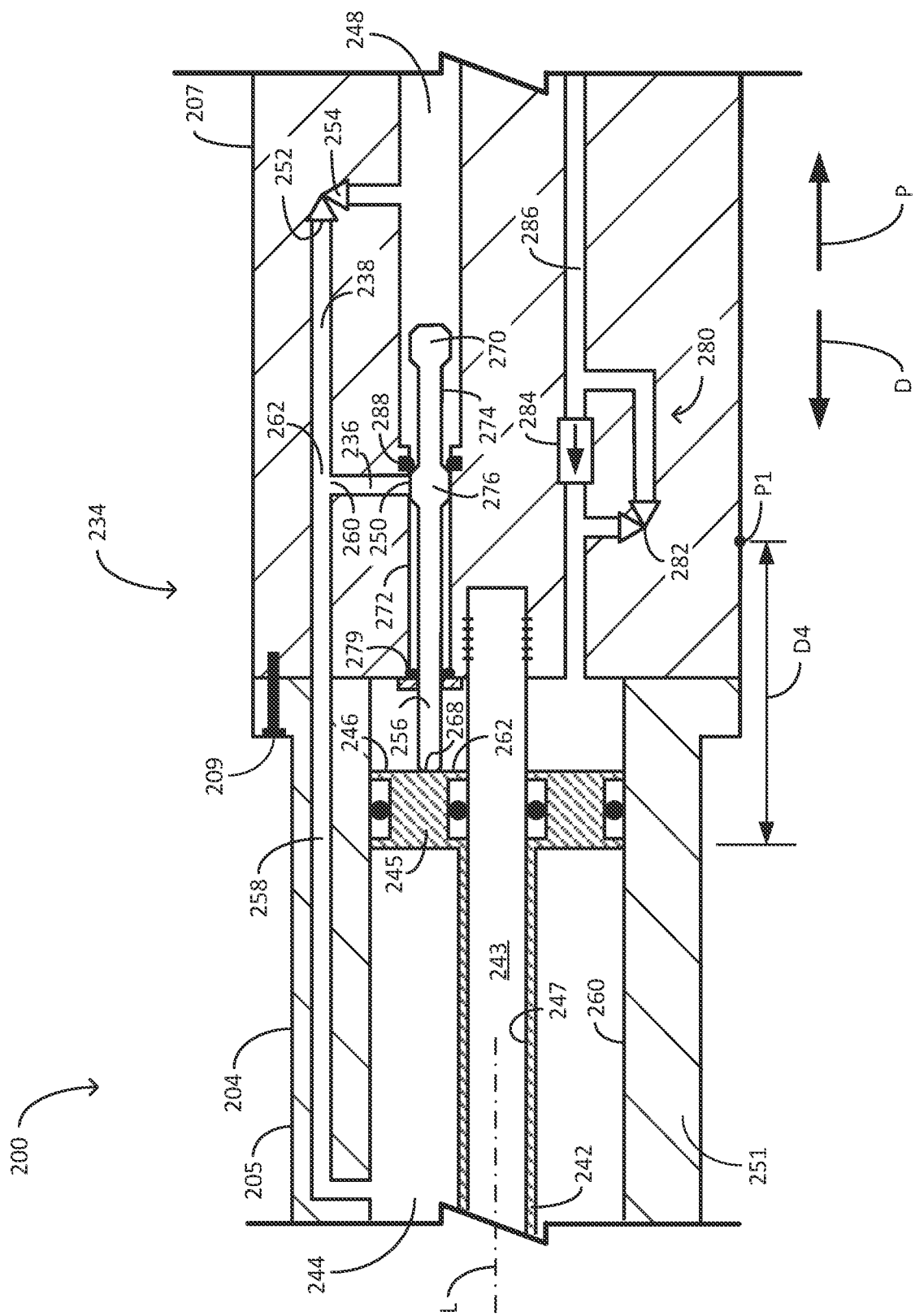
FIG. 6 is a cross-sectional illustration of the delivery system of FIG. 3 in an additional example configuration.

FIG. 6 illustrates delivery system 200 with piston 246 proximally displaced from the third piston location of FIG. 5 and having driven stop pin 256 from the third pin location to the fourth pin position. In similar manner to the second pin position (FIG. 4), as piston 246 drives stop pin 256 to the fourth pin position, some portion of stop pin 256 (e.g., second land 276) positions to block fluid flow through first inlet 250 and first fluid pathway 236. Some portion of stop pin 256 (e.g., second land 270) may be configured to seat against O-ring 288 when stop pin 256 is in the fourth pin position. With valve 254 in the closed position (e.g., with a pressure in fluid entrance pathway below a setpoint of valve 254) and stop pin 256 in the fourth pin position, fluid entrance pathway 248 is fluidly isolated from first chamber 244, and translation of piston 246 and outer shaft 242 substantially ceases. Correspondingly, when outer shaft 242 is mechanically coupled to capsule housing 128 (FIG. 1, 2), motion of capsule housing 128 relative to prosthetic heart valve device 110 substantially ceases.

In some examples, piston 246 establishes a fourth piston location within delivery system 200 when stop pin 256 is in the fourth pin position. In the fourth piston location, piston 246 defines a fourth displacement D4 between first piston face 245 and point P1 on system body 204. Fourth displacement D4 has a magnitude different from the first displacement D1 of the first piston location (FIG. 3), second displacement D2 of the second piston location (FIG. 4), and/or third displacement D3 of the third piston location (FIG. 5). In some examples, the point P1 is proximal to first piston face 245, and the fourth displacement D4 is less than the third displacement D3.

With stop pin 256 in the fourth pin position, delivery system 200 is configured to maintain piston 246 in a substantially static position relative to system body 204 until valve 254 opens to allow fluid flow from fluid entrance pathway 248 to second fluid pathway 238. For example, delivery system 200 may be configured to maintain piston 246 in the substantially static position until a pressure in fluid entrance pathway 248 exceeds a setpoint pressure of valve 254. Hence, a clinician may cause delivery system 200 to substantially maintain piston 246 in the static position (and maintain capsule housing 128 static relative to prosthetic heart valve device 110 (FIG. 1, 2)) for as long a period as desired. Further, because delivery system 200 is configured to substantially maintain the static position until the pressure in fluid entrance pathway 248 increases to the pressure setpoint of valve 254, delivery system 200 is configured to at least momentarily stop the translation of piston 246 when stop pin 256 drives to the fourth pin position. The setpoint adjustment mechanism of valve 254 may be utilized to lengthen or shorten the momentary stop when stop pin 256 drives to the fourth pin position.

In some examples, delivery system 200 establishes a second partial deployment configuration when stop pin 256 achieves the fourth pin position. In the second partial deployment configuration, delivery system 200 may be configured such that outer shaft 242 establishes capsule housing 128 in a position relative to prosthetic heart valve device 110 wherein capsule housing 128 constrains at least a portion of prosthetic heart valve device 110 (e.g., a proximal portion) from radially expanding. Outer shaft 242 may establish capsule housing 128 such that capsule housing 128 at surrounds the portion of prosthetic heart valve device 110 (e.g., the proximal portion). In some examples, the second partial deployment configuration of delivery catheter 102 is configured to limit a radial expansion of the partially unsheathed prosthetic heart valve such that the prosthetic heart valve device may be repositioned relative to a target site (e.g., to a native mitral valve).

In some examples, delivery system 200 is configured to position outer shaft 242 such that outer shaft establishes capsule housing 128 in a first position relative to prosthetic heart valve device 110 in the first partial deployment configuration (FIG. 4). Delivery system 200 may be configured to position outer shaft 242 such that outer shaft establishes capsule housing 128 in a second position relative to prosthetic heart valve device 110 in the second partial deployment configuration (FIG. 6), wherein the second position is proximal to the first position. Hence, in the second partial deployment configuration, capsule housing 128 may be more proximally withdrawn from prosthetic heart valve device 110, such that a greater portion of prosthetic heart valve device 110 is unsheathed in the second partial deployment configuration than in the first partial deployment configuration.

With delivery system 200 configured as illustrated in FIG. 6 (e.g., with stop pin 256 in the fourth pin position and valve 254 in the closed position), proximal translation of piston 246 may be re-initiated by increasing a pressure of the deployment fluid within fluid entrance pathway 248. When the pressure in fluid entrance pathway 248 increases to or above the setpoint pressure of valve 254, valve 254 may be caused to open to supply deployment fluid to first chamber 244 via second inlet 252, second fluid pathway 238, and deployment fluid conduit 258. As before, first chamber 244 is configured to direct a pressure of the deployment fluid against first piston face 245 of a piston 246, causing translation of piston 246 in the proximal direction P. Alternately, a pressure in second chamber 253 may be increased via valve 284 causing capsule housing 128 to recapture (e.g., fully or partially re-sheathe) prosthetic heart valve device 110.

Translation of piston 246 in the proximal direction P causes a translation of stop pin 256 and drives stop pin 256 from the fourth pin position to a fifth pin position. Stop pin 256 is configured to allow a flow of deployment fluid through first fluid pathway 236 in the fifth pin position. For example, translation of piston 246 may cause a proximal translation of stop pin 256, causing stop pin 256 to translate from the forth pin position wherein second land 276 blocks flow through first inlet 250 and first fluid pathway 236 to a fifth pin position wherein stop pin 256 allows flow through first inlet 250 and first fluid pathway 236.

Figure 7:
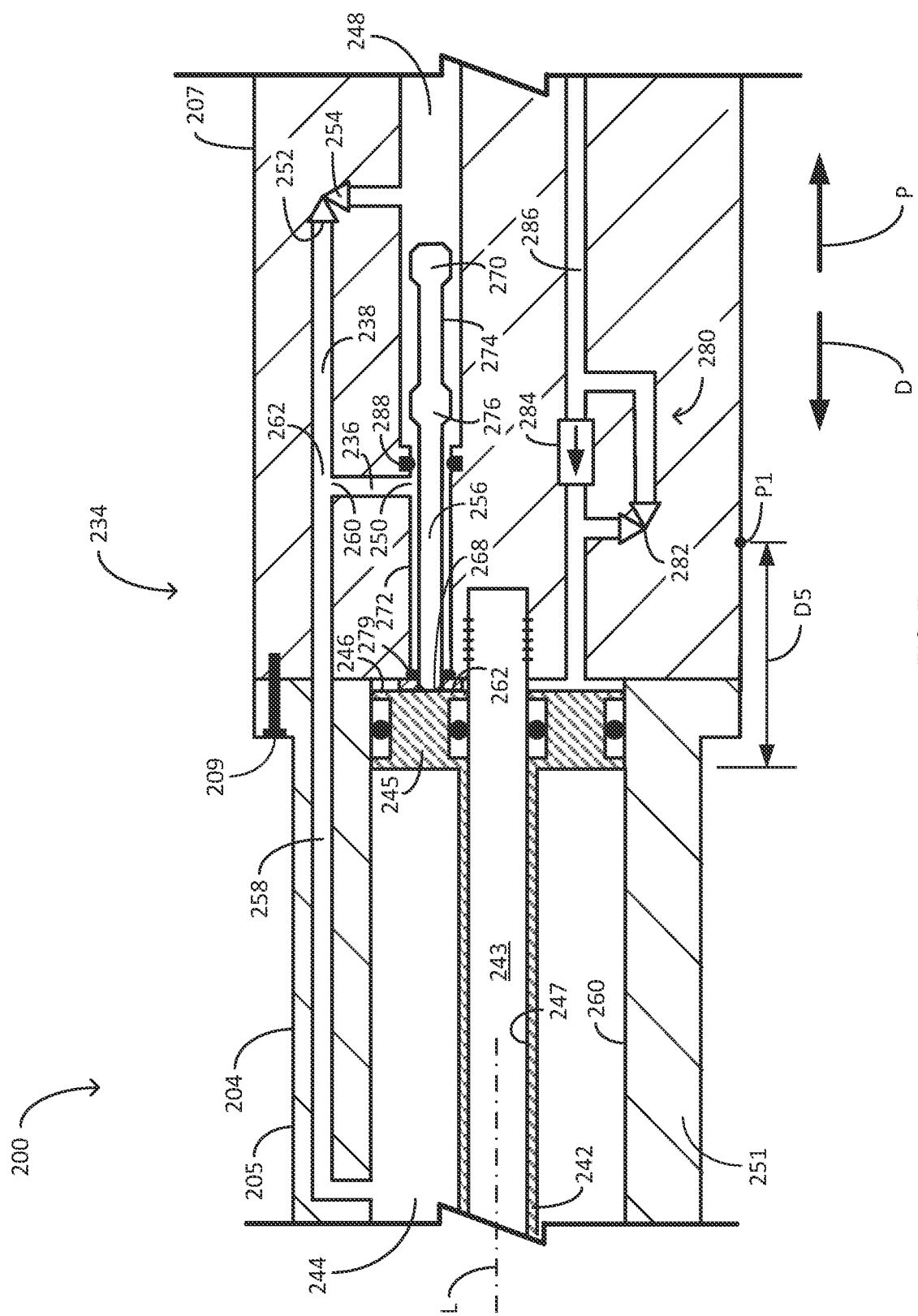
FIG. 7 is a cross-sectional illustration of the delivery system of FIG. 3 in a further configuration.

FIG. 7 illustrates delivery system 200 with piston 246 proximally displaced from the fourth piston location of FIG. 6 and having driven stop pin 256 from the fourth pin position to the fifth pin position. In the fifth pin position, stop pin 256 positions to allow flow through first inlet 250 and first fluid pathway 236. Delivery system 200 is configured to cause a decrease in the pressure in fluid entrance pathway 248 when stop pin 256 positions in the fifth pin position. For example, delivery system 200 may be configured such that a flow resistance from fluid entrance pathway 248 to first outlet 260 is less than a flow resistance from fluid entrance pathway 248 to second outlet 262 when valve 254 is open and stop pin 256 is in the fifth pin position. Valve 254 is configured to close when the pressure in fluid entrance pathway 248 is below the closing pressure of valve 254, such that delivery system 200 may provide a flow of the deployment fluid through the first fluid pathway (e.g., through first inlet 250, first fluid pathway 236, and deployment fluid conduit 258) to first chamber 244. Some portion of stop pin 256 (e.g., second land 276) may be configured to pass through the O-ring hole defined by the inner diameter of O-ring 288 when stop pin 256 translates from the fourth pin position to the fifth pin position. In some examples, second land 276 is proximal to O-ring 288 when stop pin 256 is in the fifth pin position. In some examples, land 270 is distal to O-ring 288 when stop pin 256 is in the fifth pin position.

In some examples, piston 246 assumes (e.g., translates through, or momentarily establishes) a fifth piston location within delivery system 200 when stop pin 256 is in the fifth pin position. In the fifth piston location, piston 246 defines a fifth displacement D5 between first piston face 245 and point P1 on system body 204, with the fifth displacement D5 having a magnitude different from the first displacement D1 of the first piston location (FIG. 3), the second displacement D2 of the second piston location (FIG. 4), the third displacement D3 of the third piston location (FIG. 5), and/or the fourth displacement D4 of the fourth piston location (FIG. 6). In some examples, the point P1 is proximal to first piston face 245, and the fifth displacement D5 is less than the fourth displacement D4.

Stop pin 256 may be configured to substantially remain in the fifth pin position while translating (e.g., in the proximal direction P) over some range. For example, stop pin 256 may substantially remain in the fifth pin position based on a configuration (e.g., a radius) of stop pin 256 between the most distal land (e.g., second land 276) of stop pin 256 and stop pin distal end 268. In some examples, when stop pin 256 includes an additional land distal to second land 276, stop pin 256 may substantially remain in the fifth pin position based on a width of a groove section distal to groove section 274. In some examples, the fifth pin position of stop pin 256 defines a displacement of piston 246 required to transition delivery system 200 from a partial deployment configuration (e.g., the first partial deployment configuration or the second partial deployment configuration) to a fully deployed configuration.

In some examples, delivery system 200 establishes a fully deployed configuration with stop pin 256 in the fifth pin position. Stop pin 256 may substantially remain in the fifth pin position while translating (e.g., in the proximal direction P). In the fully deployed configuration, delivery system 200 may be configured such that outer shaft 242 establishes capsule housing 128 in a position relative to prosthetic heart valve device 110 such that capsule housing 128 assumes a position whereby capsule housing 128 offers substantially no impact on the expansion of prosthetic heart valve device 110 (e.g., prosthetic heart valve device 110 is free to expand without constraint by capsule housing 128).

In some examples, in the fully deployed configuration, delivery system 200 is configured to position outer shaft 242 such that outer shaft establishes capsule housing 128 in a deployed position relative to prosthetic heart valve device 110 (e.g., as depicted in FIG. 2B). The deployed position may be proximal to the first position of the first partial deployment configuration and/or the second position of the second partial deployment configuration. Hence, in the fully deployed configuration, capsule housing 128 may be proximally withdrawn from prosthetic heart valve device 110 such that the capsule housing 128 provides no constraint to a radial expansion of prosthetic heart valve device 110.

Figure 8:
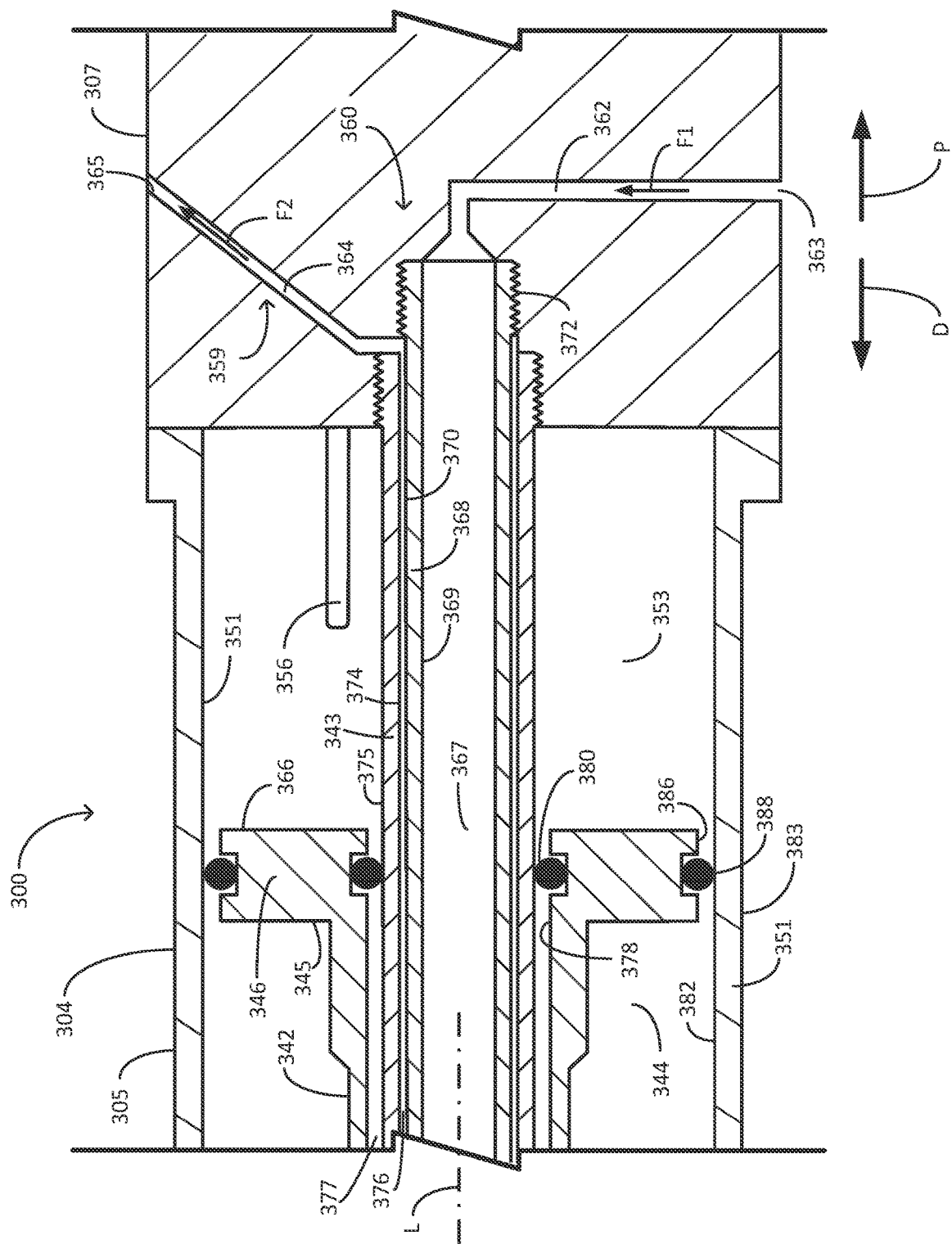
FIG. 8 is a cross-sectional illustration of an example delivery system having a flushing circuit.

The delivery system may define a flushing circuit configured to flush delivery capsule 106 and/or prosthetic heart valve device 110 (FIG. 1). For example FIG. 8 schematically illustrates a delivery system 300 defining flushing circuit 360. Delivery system 300 is an example of delivery system 200. Delivery system 300 includes system body 304 defining distal portion 305 and proximal portion 307, outer shaft 342, inner shaft 343, first chamber 344, cylinder wall 351, second chamber 353, piston 346 having first piston face 345 and second piston face 366, stop pin 356, inner peripheral surface 378, and outer peripheral surface 386, which may be configured individually and in relation to each other in the same manner as the like named components of delivery system 200. In FIG. 8, system body 304, outer shaft 342, inner shaft 343, piston 346, and cylinder wall 351 are shown in cross-section with a cutting plane taken parallel to the page.

Flushing circuit 360 is configured to provide a flushing fluid to some portion of delivery capsule 106 and/or prosthetic heart valve device 110 (FIG. 1). The flushing fluid may be used to, for example, degas some portion of delivery capsule 106. In some examples, flushing circuit 360 includes flushing pathway 362. Flushing pathway 362 may be configured to receive a supply of flushing fluid via a flushing inlet 363 defined by system body 304. System body 304 may define flushing circuit 360 such that flushing circuit 360 is fluidly isolated from first chamber 344, second chamber 353, a first fluid pathway (not shown), a second fluid pathway (not shown), and/or a recapture circuit (not shown) of delivery system 300. In some examples, flushing circuit 360 may be configured to supply a flow of flushing fluid via flushing pathway 362 in the flow direction F1.

Flushing pathway 362 may be configured to supply the flushing fluid to a central bore 367 defined by delivery system 300. In some examples, central bore 367 is defined by a conduit 368 having an interior surface 369 ("conduit interior surface 369") and an exterior surface 370 ("conduit exterior surface 370"). Central bore 367 may be defined by conduit interior surface 369. In some example, conduit interior surface 369 surrounds longitudinal axis L of delivery system 300. Conduit 368 may be configured for attachment to system body 304. For example, conduit 368 may include external threads 372 configured to threadably engage system body 304.

Conduit 368 may be configured to extend through inner shaft 343. In some examples, inner shaft 343 is a tubular shaft defining an inner channel configured to receive inner conduit 368. In some examples, inner shaft 343 includes an interior surface 374 ("inner shaft interior surface 374") and an exterior surface 375 ("inner shaft exterior surface 375"), with inner shaft interior surface 374 defining the inner channel of inner shaft 343. In some examples, inner shaft interior surface 374 surrounds conduit exterior surface 370 of conduit 368.

The delivery system may define a venting circuit configured to vent a fluid (e.g., a gas) from delivery capsule 106 and/or prosthetic heart valve device 110 (FIG. 1). For example FIG. 8 schematically illustrates delivery system 300 defining venting circuit 359. Venting circuit 359 may define a venting path for a fluid (e.g., a gas such as air) within delivery capsule 106 and/or prosthetic heart valve device 110. For example, venting circuit 359 may be used to provide a venting path for a fluid (e.g., a gas) which may become pressurized as delivery capsule 106 moves relative to prosthetic heart valve device 110. In some examples, venting circuit 359 includes venting pathway 364. Venting pathway 364 may be configured to provide a venting path via a venting outlet 365 defined by system body 304. System body 304 may define venting circuit 359 such that venting circuit 359 is fluidly isolated from first chamber 344, second chamber 353, a first fluid pathway (not shown), a second fluid pathway (not shown), and/or a recapture circuit (not shown) of delivery system 300. In some examples, venting circuit 359 may be configured to allow venting via venting pathway 364 in the flow direction F2.

In some examples, conduit exterior surface 370 and inner shaft interior surface 374 define a pathway 376 in fluid communication with venting pathway 364. Pathway 376 may define any cross-section perpendicular to longitudinal axis L. In an example, pathway 376 is an annular passage substantially surrounding longitudinal axis L. Hence, delivery system 200 may be configured to supply a flushing fluid to delivery capsule 106 and/or prosthetic heart valve device 110 via flush pathway 362 and central bore 367, and provide a venting pathway for delivery capsule 106 and/or prosthetic heart valve device 110 via pathway 376 and venting pathway 364.

Piston 346 and outer shaft 342 may define a central passage 377. Inner shaft 343 may be configured to extend through central passage 377. In some examples, inner peripheral surface 378 of piston 346 defines some portion central passage 377. In some examples, inner peripheral surface 378 at least partially surrounds a portion inner shaft exterior surface 375. Piston 346 may be configured such that inner peripheral surface 378 moves relative to inner shaft exterior surface 375 when piston 346 translates proximally or distally relative to system body 304. In some examples, inner peripheral surface 378 is configured to slidably translate over inner shaft exterior surface 375 when piston 346 translates relative to system body 304. In some examples, piston 346 is configured to hold an O-ring 380 in contact with or adjacent to inner peripheral surface 378, with O-ring 380 configured to slidably translate over inner shaft exterior surface 375 when piston 346 translates relative to system body 304. In FIG. 8, O-ring 380 is shown in cross-section with a cutting plane taken parallel to the page.

First chamber 344 may be defined by a piston cylinder defining cylinder wall 351. Cylinder wall 351 may include an inner surface 382 ("cylinder inner surface 382") and an outer surface 383 ("cylinder outer surface 383") opposite cylinder inner surface 382. Cylinder inner surface 382 may be configured to substantially surround outer peripheral surface 386 of piston 346. Cylinder wall 351 may define second chamber 353. Piston 346 may be configured such that outer peripheral surface 386 moves relative to cylinder inner surface 382 piston 346 translates proximally or distally relative to system body 304. In some examples, outer peripheral surface 386 is configured to slidably translate over cylinder inner surface 382 when piston 346 translates relative to system body 304. In some examples, piston 346 is configured to hold an O-ring 388 in contact with or adjacent to outer peripheral surface 386, with O-ring 388 configured to slidably translate over cylinder inner surface 382 when piston 346 translates relative to system body 304. In FIG. 8, O-ring 388 is shown in cross-section with a cutting plane taken parallel to the page.

Valves 254, 282, 284 may be any type of valve configured to perform the functions described herein. Valves 254, 282, 284 may be, for example, a poppet valve, a needle valve, a gate valve, a globe valve, spool valve, or some type of valve. Valves 254, 282 may be configured in any suitable manner to cause valves 254, 282 to open or partially open at a setpoint pressure and at least partially close at a closing pressure. For example, valves 254, 282 may be any type of pressure relief valve using any type of reference force element, and may be spring loaded, dome loaded, pilot valve operated, or operated in some other manner. Valve 284 may be any type of valve configured to allow a forward flow through the valve and substantially block a reverse flow through the valve. For example, valve 284 may be lift-check valve, an in-line check valve, a swing check valve, a ball check valve, a stop-check valve, or another type of non-return valve.

In some examples, operation of delivery system 200, 300 may be controlled by clinician causing a supply of deployment fluid to flow into fluid entrance pathway 248 (e.g., using fluid source 118 and fluid line 120). The clinician may cause delivery system 200, 300 to transition among the containment configuration, the first partial deployment configuration, the second partial deployment configuration, the fully deployed configuration, and/or other delivery system 200, 300 configurations through control of the supply of deployment fluid. For example, the clinician may recognize arrival at the first partial deployment configuration and/or the second partial deployment configuration by observing a pressure sensor configured to indicate a pressure in fluid entrance pathway 248. The clinician may maintain delivery system 200, 300 in the first partial deployment configuration or the second deployment configuration through control of the supply of deployment fluid. The clinician may initiate and conduct recapture operations using a recapture fluid supplied via recapture circuit 280.

In some examples, one or more aspects of delivery system 200, 300 operation may be controlled by control circuitry configured to cause an operation of delivery system 200, 300. The control circuitry may be configured to cause the supply of deployment fluid to flow into fluid entrance pathway 248 (e.g., using fluid source 118 and fluid line 120). The control circuitry may be configured to cause delivery system 200, 300 to transition among the containment configuration, the first partial deployment configuration, the second partial deployment configuration, the fully deployed configuration, and/or other delivery system 200, 300 configurations using the supply of deployment fluid. For example, the control circuitry may be configured to recognize arrival at the first partial deployment configuration and/or the second partial deployment configuration by based on a pressure signal received from a pressure sensor configured to indicate a pressure in fluid entrance pathway 248. The control circuitry may be configured to cause delivery system 200, 300 to maintain the first partial deployment configuration or the second deployment configuration using control of the supply of deployment fluid. The control circuitry may be configured to control the operations of delivery system 200, 300 based on a user input. For example, the control circuitry may be configured to transition delivery system 200, 300 among a containment configuration, a first partial deployment configuration, a second partial deployment configuration, and/or a fully deployed configuration. The control circuitry may be configured to cause the supply of recapture fluid to flow into recapture circuit 280 to initiate and/or conduct recapture operations of delivery system 200, 300 using the recapture fluid.

Figure 9:
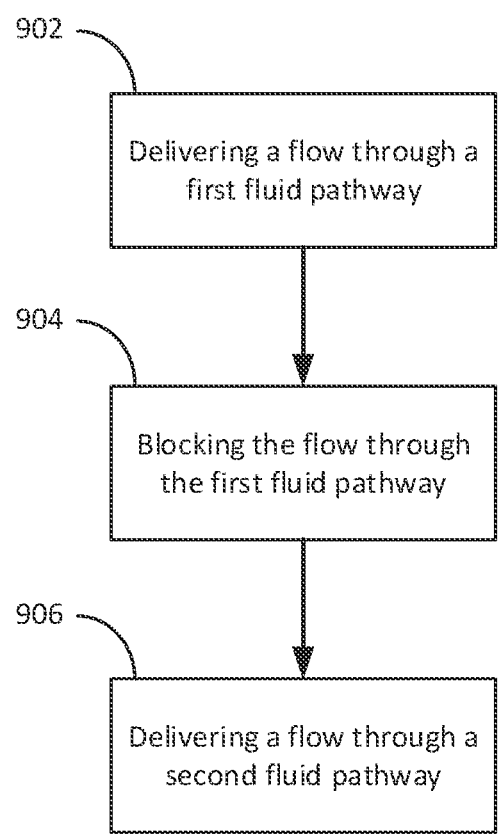
FIG. 9 is schematic flow chart for example technique for using a delivery system.

FIG. 9 illustrates a flow diagram of an example technique 1300 for deploying a prosthetic heart valve device. Although the technique is described with various reference to delivery system 100 (FIG. 1, 2), delivery system 200 (FIGS. 3, 4, 5, 6, 7), and/or delivery system 300 (FIG. 8), in other examples, the technique may be used with another delivery catheter.

The technique includes delivering a deployment fluid through first fluid pathway 236 in hydraulic circuit 234 defined by delivery system 100, 200, 300 (902). The technique may include delivering the deployment fluid to first chamber 244, 344 using first fluid pathway 236. The technique may include blocking a flow of the deployment fluid to second fluid pathway 238 using valve 254. In some examples, a first inlet 250 defined by delivery system 100, 200, 300 is in fluid communication first fluid pathway 236 and fluid entrance pathway 248, and the technique includes providing the deployment fluid to fluid entrance pathway 248. First fluid pathway 236 may be in fluid communication with deployment fluid conduit 258, with deployment fluid conduit 258 configured to deliver the deployment fluid to first chamber 244.

The technique may include causing a translating member to translate within system body 204 relative to system body 204, 304 using the deployment fluid. The translating member may be outer shaft 242, 342. The technique may include causing a capsule housing 128 to translate relative to a prosthetic heart valve device when outer shaft 242, 342 translates relative to system body 204, 304. In some examples, the technique includes causing outer shaft 242, 342 to translate by translating piston 246, 346 using a pressure of the deployment fluid. In some examples, the technique includes directing a pressure of the deployment fluid against first piston face 245, 345 of piston 246, 246 using first chamber 244, 244.

The technique includes blocking the flow of deployment fluid through the first fluid pathway (902). The technique may include causing stop pin 256, 356 to translate from a first pin position wherein stop pin 256, 356 allows the flow of the deployment fluid through first fluid pathway 236 to a second pin position wherein stop pin 256, 356 substantially blocks the flow of deployment fluid through first fluid pathway 236. Piston 246, 346 may be configured such that translation of piston 246, 346 causes translations of stop pin 256, 256 from the first pin position to the second pin position. The technique may include transitioning delivery system 200, 300 from a containment configuration to a first partial deployment configuration as stop pin 256, 356 transitions from the first pin position to the second pin position. The technique may include transitioning piston 246, 346 from a first piston location to a second piston location to transition stop pin 256, 356 from the first pin position to the second pin position. The technique may include venting a fluid from second chamber 253, 353 as piston 246, 346 translates relative to system body 204, 304.

The technique includes delivering a deployment fluid through second fluid pathway 238 in hydraulic circuit 234 defined by delivery system 100, 200, 300 (906). The technique may include delivering the deployment fluid to first chamber 244, 344 using second fluid pathway 236. The technique may include allowing a flow of the deployment fluid to second fluid pathway 238 using valve 254. In some examples, the technique includes increasing a pressure in fluid entrance pathway 248 to cause valve 254 to open and allow the flow of deployment fluid to second fluid pathway 238. In some examples, a second inlet 252 defined by delivery system 100, 200, 300 is in fluid communication second fluid pathway 238 and fluid entrance pathway 248 when valve 254 is opened, and the technique includes providing the deployment fluid to fluid entrance pathway 248. Second fluid pathway 238 may be in fluid communication with deployment fluid conduit 258, with deployment fluid conduit 258 configured to deliver the deployment fluid to first chamber 244.

The technique may include causing stop pin 256, 356 to translate from the second pin position wherein stop pin 256, 356 substantially blocks the flow of the deployment fluid through first fluid pathway 236 to a third pin position wherein stop pin 256, 356 allows the flow of deployment fluid through first fluid pathway 236. Piston 246, 346 may be configured such that translation of piston 246, 346 causes translations of stop pin 256, 256 from the second pin position to the third pin position. The technique may include transitioning piston 246, 346 from the second piston location to a third piston location to transition stop pin 256, 356 from the second pin position to the third pin position. In some examples, the technique includes reducing a pressure in fluid entrance pathway 248 with stop pin 256, 256 in the third pin position and causing valve 254 to shut using the reduced pressure.

In some examples, the technique includes blocking the flow of deployment fluid through the first fluid pathway by causing stop pin 256, 356 to translate from the third pin position wherein stop pin 256, 356 allows the flow of the deployment fluid through first fluid pathway 236 to a fourth pin position wherein stop pin 256, 356 substantially blocks the flow of deployment fluid through first fluid pathway 236. Piston 246, 346 may be configured such that translation of piston 246, 346 causes translations of stop pin 256, 256 from the third pin position to the fourth pin position. The technique may include transitioning delivery system 200, 300 to a second partial deployment configuration as stop pin 256, 356 transitions from the third pin position to the fourth pin position.

The technique may include delivering the deployment fluid through second fluid pathway 238 when stop pin 256, 356 is in the fourth pin position. The technique may include allowing a flow of the deployment fluid to second fluid pathway 238 using valve 254 when stop pin 256, 356 is in the fourth pin position. In some examples, the technique includes increasing a pressure in fluid entrance pathway 248 to cause valve 254 to open and allow the flow of deployment fluid to second fluid pathway 238 when stop pin 256, 356 is in the fourth pin position.

The technique may include causing stop pin 256, 356 to translate from the fourth pin position wherein stop pin 256, 356 substantially blocks the flow of the deployment fluid through first fluid pathway 236 to a fifth pin position wherein stop pin 256, 356 allows the flow of deployment fluid through first fluid pathway 236. Piston 246, 346 may be configured such that translation of piston 246, 346 causes translations of stop pin 256, 256 from the fourth pin position to the fifth pin position. In some examples, the technique includes transitioning piston 246, 346 from the fourth piston location to a full deployment position. In some examples, the technique includes reducing a pressure in fluid entrance pathway 248 with stop pin 256, 256 in the fifth pin position and causing valve 254 to shut using the reduced pressure. The technique may include transitioning delivery system 200, 300 to fully deployed configuration with stop pin 256, 356 in the fifth pin position.

The Present Disclosure Includes the Following Examples:

Example 1

A system for a prosthetic device, the system comprising: a delivery system configured to be hydraulically driven between a containment configuration for holding the prosthetic device and a deployment configuration for at least partially deploying the prosthetic device, wherein the delivery system defines a hydraulic circuit including a first fluid pathway and a second fluid pathway, wherein the delivery system is configured such that a hydraulic delivery of a deployment fluid along the first fluid pathway: drives the delivery system from the containment configuration towards the deployment configuration, and drives a stop pin from a first pin position in which the deployment fluid flows along the first fluid pathway to a second pin position in which the deployment fluid is blocked from flowing along the first fluid pathway, wherein when the stop pin is in the second pin position, the deployment fluid is directed through the second flow pathway.

Example 2

The system of example 1, wherein the hydraulic circuit is configured to drive the stop pin from the second pin position to a third pin position when the deployment fluid is directed through the second flow pathway, and wherein hydraulic circuit is configured to direct the deployment fluid along the first fluid pathway when the stop pin is in the third pin position.

Example 3

The system of example 1 or 2, wherein the delivery system includes a system body and a translating member, the translating member configured to translate relative to the system body, and wherein the delivery system is configured such that the hydraulic delivery of the deployment fluid along the first fluid pathway or the second fluid pathway translates the translating member in a first direction relative to the system body.

Example 4

The system of example 3, wherein the translating member is configured to drive the stop pin from the first pin position to the second pin position when the translating member translates in the first direction relative to the system body.

Example 5

The system of example 3 or 4, further comprising a recapture circuit, wherein a hydraulic delivery of a recapture fluid along the recapture circuit translates the translating member in a second direction relative to the system body, wherein the second direction is opposite the first direction.

Example 6

The system of example 5, wherein the translating member comprises a piston, wherein the piston is configured to fluidly isolate the first fluid pathway from the recapture fluid circuit and fluidly isolate the second fluid pathway from the recapture fluid circuit.

Example 7

The system of any of examples 1-6, wherein the first fluid pathway and the second fluid pathway are configured for fluid communication with an fluid entrance pathway, and wherein a valve is configured to direct the deployment fluid to the second fluid pathway when a pressure in the fluid entrance pathway exceeds a pressure setpoint.

Example 8

The system of any of examples 1-7, wherein the delivery system is configured to hold the prosthetic device in the first deployment configuration when the stop pin is in the second pin position and until a valve directs the deployment fluid through the second fluid pathway.

Example 9

The system of any of examples 1-8, wherein the first fluid pathway and the second fluid pathway are in fluid communication with an entrance fluid pathway, and wherein the stop pin is configured to fluidly isolate the first fluid pathway and the entrance fluid section when the stop pin is in the second pin position.

Example 10

The system of any of examples 1-9, further comprising a recapture fluid circuit, wherein the delivery system is configured such that delivery of a recapture fluid along the recapture fluid circuit drives the delivery system from the first deployment configuration towards the containment configuration.

Example 11

The system of any of examples 1-10, further comprising a recapture fluid circuit, wherein the recapture circuit is configured to vent a section of the delivery system via a valve when the delivery system delivers the deployment fluid to at least one of the first fluid pathway or the second fluid pathway.

Example 12

The system of any of examples 1-11, further comprising a flushing fluid pathway configured to deliver a flushing fluid to the prosthetic device, wherein the flushing fluid pathway is fluidly isolated from the first fluid pathway, the second fluid pathway, and the recapture circuit at least when the delivery system directs the deployment fluid along the first fluid pathway or the second fluid pathway.

Example 13

The system of any of examples 1-12, wherein the stop pin is configured to slidably translate within the first fluid pathway when the delivery system drives the stop pin from the first pin position to the second pin position.

Example 14

The system of any of examples 1-13, wherein the hydraulic circuit is configured to drive the stop pin from the second pin position to a third pin position in which the deployment fluid flows through the first fluid pathway, and the hydraulic circuit is configured to drive the stop pin from the third pin position to a fourth pin position, wherein in the fourth pin position the deployment fluid is directed via a valve through the second flow pathway.

Example 15

The system of examples 14, wherein the delivery system is configured to hold the prosthetic device in a second deployment configuration when the stop pin is in the third pin position and until the valve directs the deployment fluid through the second fluid pathway.

Example 16

A system for a prosthetic device comprising: a delivery system configured to be hydraulically driven between a containment configuration for holding the prosthetic device and a deployment configuration for at least partially deploying the prosthetic device, wherein the delivery system defines a hydraulic circuit including a first fluid pathway and a second fluid pathway, wherein the delivery system is configured such that a hydraulic delivery of a deployment fluid along the first fluid pathway: drives the delivery system from the containment configuration towards a first deployment configuration, and drives a stop pin from a first pin position in which the deployment fluid flows along the first fluid pathway to a second pin position in which the deployment fluid is blocked from flowing along the first fluid pathway, wherein when the stop pin is in the second pin position, the deployment fluid is directed via a valve through the second flow pathway, wherein the delivery system is configured to hold the prosthetic device in the first deployment configuration when the stop pin is in the second pin position, at least until the valve directs the deployment fluid through the second fluid pathway, and wherein the delivery system is configured to drive the stop pin from the second pin position to a third pin position in which the deployment fluid flows along the first fluid pathway.

Example 17

The system of example 16, further comprising a recapture fluid circuit, wherein the recapture circuit is configured to vent a section of the delivery system via a second valve when the delivery system delivers the deployment fluid to at least one of the first fluid pathway and the second fluid pathway.

Example 18

The system of example 17, further comprising a recapture fluid circuit, wherein the delivery system is configured such that delivery of a recapture fluid along the recapture fluid circuit drives the delivery system from the first deployment configuration towards the containment configuration.

Example 19

A method of deploying a prosthetic device, the method comprising: delivering a fluid flow through a first fluid pathway in a hydraulic circuit defined by a delivery system; driving the delivery system from a containment configuration toward a first deployment configuration using the fluid flow through the first fluid pathway; driving a stop pin from a first pin position to a second pin position using the fluid flow through the first fluid pathway; blocking the fluid flow through the first fluid pathway using the stop pin in the second pin position and directing a fluid flow through a second fluid pathway in the hydraulic circuit; and driving the delivery system toward a deployment configuration using the fluid flow through a second fluid pathway.

Example 20

The method of example 19, further comprising venting the delivery system using a recapture fluid circuit defined by the delivery system and fluidly isolated from the first fluid pathway and the second fluid pathway.

Various examples have been described. These examples are not meant to limit the scope of the following claims.

What is claimed is:

1. A system for a prosthetic device, the system comprising:
a delivery system configured to be hydraulically driven between a containment configuration for holding the prosthetic device and a deployment configuration for at least partially deploying the prosthetic device,
wherein the delivery system defines a hydraulic circuit including a first fluid pathway and a second fluid pathway,
wherein the delivery system is configured such that a hydraulic delivery of a deployment fluid along the first fluid pathway:
drives the delivery system from the containment configuration towards the deployment configuration, and
drives a stop pin from a first pin position in which the deployment fluid flows along the first fluid pathway to a second pin position in which the deployment fluid is blocked from flowing along the first fluid pathway, wherein when the stop pin is in the second pin position, the deployment fluid is directed through the second flow pathway.

2. The system of claim 1, wherein the hydraulic circuit is configured to drive the stop pin from the second pin position to a third pin position when the deployment fluid is directed through the second flow pathway, and wherein hydraulic circuit is configured to direct the deployment fluid along the first fluid pathway when the stop pin is in the third pin position.

3. The system of claim 1, wherein the delivery system includes a system body and a translating member, the translating member configured to translate relative to the system body, and wherein the delivery system is configured such that the hydraulic delivery of the deployment fluid along the first fluid pathway or the second fluid pathway translates the translating member in a first direction relative to the system body.

4. The system of claim 3, wherein the translating member is configured to drive the stop pin from the first pin position to the second pin position when the translating member translates in the first direction relative to the system body.

5. The system of claim 3, further comprising a recapture circuit, wherein a hydraulic delivery of a recapture fluid along the recapture circuit translates the translating member in a second direction relative to the system body, wherein the second direction is opposite the first direction.

6. The system of claim 5, wherein the translating member comprises a piston, wherein the piston is configured to fluidly isolate the first fluid pathway from the recapture fluid circuit and fluidly isolate the second fluid pathway from the recapture fluid circuit.

7. The system of claim 1, wherein the first fluid pathway and the second fluid pathway are configured for fluid communication with an fluid entrance pathway, and wherein a valve is configured to direct the deployment fluid to the second fluid pathway when a pressure in the fluid entrance pathway exceeds a pressure setpoint.

8. The system of claim 1, wherein the delivery system is configured to hold the prosthetic device in the first deployment configuration when the stop pin is in the second pin position and until a valve directs the deployment fluid through the second fluid pathway.

9. The system of claim 1, wherein the first fluid pathway and the second fluid pathway are in fluid communication with an entrance fluid pathway, and wherein the stop pin is configured to fluidly isolate the first fluid pathway and the entrance fluid section when the stop pin is in the second pin position.

10. The system of claim 1, further comprising a recapture fluid circuit, wherein the delivery system is configured such that delivery of a recapture fluid along the recapture fluid circuit drives the delivery system from the first deployment configuration towards the containment configuration.

11. The system of claim 1, further comprising a recapture fluid circuit, wherein the recapture circuit is configured to vent a section of the delivery system via a valve when the delivery system delivers the deployment fluid to at least one of the first fluid pathway or the second fluid pathway.

12. The system of claim 1, further comprising a flushing fluid pathway configured to deliver a flushing fluid to the prosthetic device, wherein the flushing fluid pathway is fluidly isolated from the first fluid pathway, the second fluid pathway, and the recapture circuit at least when the delivery system directs the deployment fluid along the first fluid pathway or the second fluid pathway.

13. The system of claim 1, wherein the stop pin is configured to slidably translate within the first fluid pathway when the delivery system drives the stop pin from the first pin position to the second pin position.

14. The system of claim 1, wherein the hydraulic circuit is configured to drive the stop pin from the second pin position to a third pin position in which the deployment fluid flows through the first fluid pathway, and
the hydraulic circuit is configured to drive the stop pin from the third pin position to a fourth pin position, wherein in the fourth pin position the deployment fluid is directed via a valve through the second flow pathway.

15. The system of claim 14, wherein the delivery system is configured to hold the prosthetic device in a second deployment configuration when the stop pin is in the third pin position and until the valve directs the deployment fluid through the second fluid pathway.

16. A system for a prosthetic device comprising:
a delivery system configured to be hydraulically driven between a containment configuration for holding the prosthetic device and a deployment configuration for at least partially deploying the prosthetic device,
wherein the delivery system defines a hydraulic circuit including a first fluid pathway and a second fluid pathway,
wherein the delivery system is configured such that a hydraulic delivery of a deployment fluid along the first fluid pathway:
drives the delivery system from the containment configuration towards a first deployment configuration, and
drives a stop pin from a first pin position in which the deployment fluid flows along the first fluid pathway to a second pin position in which the deployment fluid is blocked from flowing along the first fluid pathway, wherein when the stop pin is in the second pin position, the deployment fluid is directed via a valve through the second flow pathway,
wherein the delivery system is configured to hold the prosthetic device in the first deployment configuration when the stop pin is in the second pin position, at least until the valve directs the deployment fluid through the second fluid pathway, and
wherein the delivery system is configured to drive the stop pin from the second pin position to a third pin position in which the deployment fluid flows along the first fluid pathway.

17. The system of claim 16, further comprising a recapture fluid circuit, wherein the recapture circuit is configured to vent a section of the delivery system via a second valve when the delivery system delivers the deployment fluid to at least one of the first fluid pathway and the second fluid pathway.

18. The system of claim 17, further comprising a recapture fluid circuit, wherein the delivery system is configured such that delivery of a recapture fluid along the recapture fluid circuit drives the delivery system from the first deployment configuration towards the containment configuration.

19. A method of deploying a prosthetic device, the method comprising:
delivering a fluid flow through a first fluid pathway in a hydraulic circuit defined by a delivery system;
driving the delivery system from a containment configuration toward a first deployment configuration using the fluid flow through the first fluid pathway;
driving a stop pin from a first pin position to a second pin position using the fluid flow through the first fluid pathway;
blocking the fluid flow through the first fluid pathway using the stop pin in the second pin position and directing a fluid flow through a second fluid pathway in the hydraulic circuit; and
driving the delivery system toward a deployment configuration using the fluid flow through a second fluid pathway.

20. The method of claim 19, further comprising venting the delivery system using a recapture fluid circuit defined by the delivery system and fluidly isolated from the first fluid pathway and the second fluid pathway.

* * * * *